(12) United States Patent
Lussana et al.

(10) Patent No.: US 7,034,159 B2
(45) Date of Patent: Apr. 25, 2006

(54) PHARMACEUTICAL COMPOSITIONS COMPRISING 1-ISOPROPYL-3-[(4-M-TOLUIDINO-3-PYRIDYL)SULPHONYL]-UREA AS ACTIVE INGREDIENT

(75) Inventors: Massimiliano Lussana, Gorle (IT); Mauro Rainoni, Cernusco Sul Naviglio (IT)

(73) Assignee: Cosma S.p.A., Ciserano (IT)

( * ) Notice: Subject to any disclaimer, the term of this patent is extended or adjusted under 35 U.S.C. 154(b) by 399 days.

(21) Appl. No.: 10/400,890

(22) Filed: Mar. 27, 2003

(65) Prior Publication Data

US 2003/0187032 A1    Oct. 2, 2003

(30) Foreign Application Priority Data

Mar. 27, 2002 (IT) .......................... MI2002A0639

(51) Int. Cl.
*C07D 213/70* (2006.01)
*A61K 31/44* (2006.01)

(52) U.S. Cl. .................... 546/294; 546/293; 514/347

(58) Field of Classification Search ................ 546/293, 546/294; 514/347
See application file for complete search history.

(56) References Cited

U.S. PATENT DOCUMENTS

| | | | |
|---|---|---|---|
| 4,743,693 A | 5/1988 | Topfmeier et al. | |
| 4,822,807 A | 4/1989 | Topfmeier et al. | |
| 6,482,417 B1 * | 11/2002 | Leibovici et al. | ........... 424/400 |
| 2002/0035135 A1 | 3/2002 | Leibovici et al. | |

FOREIGN PATENT DOCUMENTS

WO    WO 02/067935 A1    9/2002

* cited by examiner

*Primary Examiner*—Raymond Henley, III
*Assistant Examiner*—Donna Jagoe
(74) *Attorney, Agent, or Firm*—Mayer, Brown, Rowe & Maw LLP; Joseph A. Mahoney; Jamison E. Lynch

(57) ABSTRACT

The present invention concerns the use of 1-isopropyl-3-[(4-m-toluidino-3-pyridyl)sulphonyl]-urea in the pharmaceutical field. In particular, it proposes the use of a pure and stable polymorphic form of 1-isopropyl-3-[(4-m-toluidino-3-pyridyl)sulphonyl]-urea for the preparation of solid pharmaceutical forms, and likewise a method of synthesis to obtain such a pure and stable polymorphic form of 1-isopropyl-3-[(4-m-toluidino-3-pyridiyl)sulphonyl]-urea.

1 Claim, 26 Drawing Sheets

US 7,034,159 B2

PHARMACEUTICAL COMPOSITIONS COMPRISING 1-ISOPROPYL-3-[(4-M-TOLUIDINO-3-PYRIDYL)SULPHONYL]-UREA AS ACTIVE INGREDIENT

CROSS REFERENCE TO RELATED APPLICATIONS

This application claims the benefit of Italian Patent Application No. MI2002A000639, filed Mar. 27, 2002, and is hereby incorporated by reference to the extent permitted by law.

FIELD OF THE INVENTION

The present invention concerns pharmaceutical compositions comprising 1-isopropyl-3-[(4-m-toluidino-3-pyridyl) sulphonyl]-urea as active ingredient.

BACKGROUND OF INVENTION

Torsemide (or torasemide), namely 1-isopropyl-3-[(4-m-toluidino-3-pyridyl)sulphonyl]-urea or N-[[(1-methylethyl) amino]carbonyl]-4-[(3-methylphenyl)amino]-3-pyridine-sulphonamide, or 3-isopropylcarbamylsulphonamide-4-(3'-methylphenyl)aminopyridine, $C_{16}H_{20}N_4O_3S$, m.w. 348.43, CAS Nr. 56211-40-6, described for the first time in example 71 of the West German Patent DE 25 16 025 dating from 1974, is a compound which has well known applicability in the pharmaceutical field, in particular for the manufacture of diuretic agents. Recently, torsemide has also been proposed for the treatment of cerebral edema (U.S. Pat. No. 5,486,530).

Like many molecules of organic nature, also torsemide shows the phenomenon of polymorphism (the existence of various crystalline modifications) in the solid state, which makes the preparation of solid pharmaceutical forms of it particularly problematic. As is well known to experts in the art, polymorphic forms of a compound demonstrate, by means of their different crystalline structure, distinct physico-chemical characteristics (amongst which not only thermodynamic stability, but also the kinetic characteristics), amongst which, purely by means of example, solubility, with obvious respective consequences on the resulting pharmacokinetics. It can thus occur that some polymorphic forms of a given compound are particularly suited to the preparation of specific solid pharmaceutical formulations with defined characteristics, for example bioavailability in patients, whilst other polymorphic forms instead require completely different formulations or are even unusable. Despite the fact that, clearly, every polymorphic form is characterised by its thermodynamic stability which distinguishes it from the others, the synthesis reactions and the purification treatments used in industry in practice always take place under kinetically controlled conditions, frequently favouring the formation, at least partially, of metastable polymorphic forms. For the expert in the art wishing to formulate pharmaceutical compositions with highly reproducible pharmacokinetics, it is therefore critical not only to understand the single polymorphs of a compound but also their formation conditions in the different synthesis reactions and in the various contemplatable purification methods, because certain polymorphs or mixtures of various polymorphs are frequently poorly suited or poorly usable to its ends. Scrupulous study of the conditions of formation of the various polymorphic forms is also necessary with reference to the storage of the raw materials, in that, according to the relative metastability and following unpredictable interactions, transformations between various polymorphs are also possible downstream of the procedures primarily applied to the attainment of the active ingredient in pure form.

Consequently, following the discovery of the polymorphy of torsemide, numerous and great efforts have been invested by various groups of researchers to explore its single polymorphic forms, the usability of these polymorphic forms in the pharmaceutical field and, last but not least, the conditions which lead to the formation of certain polymorphic forms in certain environments.

For example, in the American Patents re-issue 34,672 and re-issue 34,580, which date from 1985, are described a form I and a form II of torsemide characterised amongst others, respectively, by a melting point interval between approx. 159° C. and approx 161.5° C. for form I and a melting point interval of between approx. 157.5° C. and approx. 160° C. for form II. In particular, a method for the attainment of form I of torsemide in pure form, suitable for the production of solid pharmaceutical forms is also described.

Further verifications have been carried out, independently, in 1994, by a group of Japanese researchers which in the context of a "review" appearing in a scientific magazine ("Chemical structure and physico-chemical properties of torasemide", Kondo et al. Iyakuhin Kenkyu, Vol. 25, No. 9 (1994)) have carried out very deep physico-chemical studies and have acquired very detailed analytical data on samples of torsemide. New methods of synthesis for various forms of torsemide have also been proposed, then characterised in a very complete manner within the scope of this study. The polymorphic form II of torsemide described in this work is obtained from crude torsemide which is dissolved according to well defined proportions (1:16) in water which is then alkalinised with aqueous solutions of sodium hydroxide until reaching a pH of 10. Later, the pH is lowered by the addition of acetic acid until neutralised (pH 7), and the crystals thus obtained are filtered. In addition, it has been found that it is possible to obtain a pure form I of torsemide from this form II by the resuspension of the crystals of form II in a defined quantity of water with subsequent agitation over 20 days at room temperature. With the objective of exploration of the applicability of the various forms of torsemide for the manufacture of pharmaceutical products, the authors of this article have also explored the relative stability of the polymorphic form I and form II obtained according to their method. Whilst form I has been judged sufficiently stable, form II has instead been held to be poorly stable because it is susceptible to humidity, in that it (auto)-transforms into form I in the presence of just water. As a consequence, it has been concluded by Kondo et al. that form II of torsemide obtained and studied by them is not suitable for the preparation of solid pharmaceutical forms.

Over the following years, various groups have then independently identified further polymorphic forms of torsemide, and have studied the characteristics let alone the conditions for their attainment and they have also proposed them validly usable as active ingredients in the preparation of pharmaceutical compositions. Despite all this work, in part also very recently, and despite the notable amount of data recorded and studies completed, the only polymorphic form of torsemide actually used in the pharmaceutical field up to now in the form of solid administrations, is the form I of torsemide, specifically that described in the American Patent Reissue 34,580 and Reissue 34,672.

In fact, up until a short time ago, torsemide was not quoted in any Pharmacopoeia in the world. Torsemide is entered in the US Pharmacopoeia only in the ambit of the edition published in 2001 (USP25) and valid from January 2002 onwards, whilst the only official specification available up to then which provided instructions on the characteristics of torsemide for use as an active ingredient in pharmaceutical preparations was a monograph published during the Pharmacopeial Forum 26, No. 3, then updated ad Pharmacopeial Forum 26, No. 5. It is important to note that in USP 25 and in the preceding monographs, reference is made exclusively to form I of torsemide, but the relative reference standard, was not—and is still not—available in that it is still missing from the official catalogue of the "USP and FCC Reference Standards and USP Authentic Substances", including the November–December 2001 edition. The availability of the standard does not even appear in the $1^{st}$ Supplement to the USP which will be official from the $1^{st}$ Apr. 2002.

From the above, it is clear that 27 years after the discovery of torsemide, and despite the considerable amount of additional polymorphic forms described, the only polymorphic form effectively used in the pharmaceutical field for the preparation of solid formulations is the form I of torsemide as it is described in the American Patent Reissue 34,580 and Reissue 34,672.

On the other hand, it is known however that the solubility of form I is not optimal with respect to that of the other polymorphs, which is reflected amongst others also in the pharmacokinetic characteristics of the respective solid pharmaceutical forms containing form I of torsemide, and therefore the availability of new pharmaceutical forms which contain other polymorphs of torsemide which show greater solubility is highly desirable. The satisfaction of such an objective is the subject of the present invention.

SUMMARY OF INVENTION

To overcome the problems of the known art, and in particular to obtain solid pharmaceutical forms of torsemide containing an active ingredient characterised by very high solubility, according to a first aspect, the present invention proposes the use of pure and stable form II of torsemide for the preparation of solid pharmaceutical forms. Thus doing, one obtains new solid pharmaceutical compositions containing form II of 1-isopropyl-3-[(4-m-toluidino-3-pyridyl)sulphonyl]-urea as active ingredient.

A further aspect of the present invention is the availability of a procedure which guarantees making available pure and stable form II of torsemide as above from crude torsemide with high yield and with very high reproducibility.

A further aspect of the present invention is the provision of an analytical method able to determine whether a given preparation of torsemide form II is pure and stable.

DESCRIPTION OF THE FIGURES

The invention, as described in the ambit of the present patent application is further illustrated by the following Figures in which, in the following descriptions of the graphical representations, the "Y" axis is intended as the vertical axis of the graph and the "X" axis is intended as the horizontal axis of the graph.

DETAILED DESCRIPTION OF THE INVENTION

Within the ambit of the present invention, it has been surprisingly found that pure form II of torsemide, as described and characterised in the works by Kondo et al., is also stable over long-term storage and under conditions of high humidity, which render it suitable for the preparation of solid pharmaceutical forms which derive the advantage of the increased solubility of form II of torsemide. Such a finding is unexpected, in that Kondo et al. had instead concluded that form II of torsemide auto-transformed itself into form I in the presence of humidity, with the consequence that the attainment of a stable form II over time, at least under realistically operable storage conditions with reasonable economic efforts in the distribution of active ingredients and pharmaceutical products, had been judged virtually impossible. In fact, on the basis of the considerations made by Kondo et al., one concludes that form II, with passing time, would have remained at least partially "contaminated" by form I, at least if the production and the distribution of form II of torsemide, let alone the preparation of solid pharmaceutical forms obtainable from it and their distribution and their storage (both by the reseller, and by the patient such as the "end consumer"), had not taken place under strictly anhydrous conditions.

Figure 11:
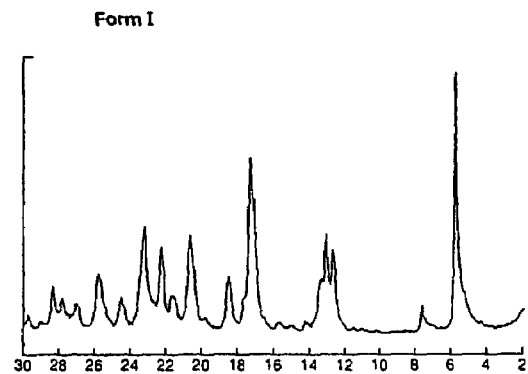
FIG. 11: X-ray diffractogram of powders of form I of torsemide as published by Kondo et al. in Iyakuhin Kenkyu Vol. 25 No. 9 (1994). On the Y axis is represented the intensity, whilst the X axis reports the angle of reflection (in degrees 2 theta) decreasing from left to right.

The inventors of the present Patent application have found however that form II of torsemide, as it was already characterised in a more general manner in Kondo et al., and in particular in its pure and stable form, for example obtainable through the procedure described in the present patent application, is instead satisfactorily inert during long periods of storage, even in conditions of high humidity. Consequently form II of torsemide is not susceptible (under usual storage conditions) to auto-transformation into form I and therefore form II is suitable for the preparation of solid pharmaceutical forms. In addition, the inventors of the present invention have also perfected a new particularly preferred method of synthesis which produces pure and stable form II of torsemide, suitable for the preparation of solid pharmaceutical forms with high yields and optimum reproducibility. In particular, according to the method of synthesis found by the inventors of the present patent application, one obtains very high yields of pure and stable form II of torsemide, namely 96% or greater with respect to crude torsemide. In order to study in detail the characteristics of forms I and II of torsemide and of their reciprocal transformations, and in the absence of standard samples and/or "official" data (not available from the USP), form I and form II discussed in the present patent application have been identified with reference to the above mentioned article by Kondo et al. ("Chemical structure and physico-chemical properties of torasemide", Kondo et al. Iyakuhin Kenkyu, Vol 25, No. 9 (1994) in which are published the X-ray diffractograms of powders of form II of torsemide (FIG. 1) and of form I of torsemide (FIG. 11) registered on a Siemens D500 powder diffractometer, as well as the relative FT—IR spectra-registered on a Perkin Elmer 320 spectrophotometer—of both polymorphic forms (FIG. 2).

The inventors of the present patent application have obtained form I and form II of torsemide from crude torsemide by following the general strategy proposed by Kondo et al. and have studied in detail the differences which appear between form I and form II of torsemide in the respective X-ray diffractograms (registered on a PW 1700 diffractometer) and also in the FT-IR spectra registered in KBr (with FT-IR apparatus obtainable from Jasco and from Perkin Elmer) and have found that, in particular through the analysis of the relative FT-IR spectra in KBr it is possible to still observe contaminations of 1% (by weight) of form I of torsemide in a sample composed of form II of torsemide. The applicability and universality of such a method of detection of small quantities of form I of torsemide in a sample of form II of torsemide which is based on the evaluation of the presence or absence of a peak at approx. 1697 $cm^{-1}$, characteristic of the FT-IR spectra of form I of torsemide, has been verified on two FT-IR spectrophotometers supplied by different manufacturers (Perkin Elmer and Jasco). It has thus been found that the detection method which is based on such an evaluation of the FT-IR spectrum in KBr is markedly more sensitive than the evaluation of the relative X-ray diffractograms of the powders, in that the detection limits of small amounts of form I of torsemide in a sample of form II of torsemide, in particular on the basis of the presence or absence of a signal at approx. 5.7° two theta present exclusively in the -ray diffractogram of the powders of form I of torsemide (see FIGS. 11 and 12) is only 2% (by weight). Consequently, with the method of detection of very small contaminations of form I of torsemide in a sample of form II of torsemide which is based on the evaluation of the presence of a peak at approx. 1697 $cm^{-1}$ in the FT-IR spectrum, used and described in the present patent application request, the inventors have studied and perfected, for the first time, an analytical means of greater sensitivity, also then used for the verification of the progress of the stability tests according to the ICH (Q1A, "Stability testing of new Drug Substances and new Drug Products", $1^{st}$ edition Oct. 27, 1997 and $2^{nd}$ edition Nov. 8, 2000) to which have been subjected 3 samples of pure form II of torsemide, to allow the observation of even minimal variations of the polymorphic composition of a sample over time.

Figure 1:
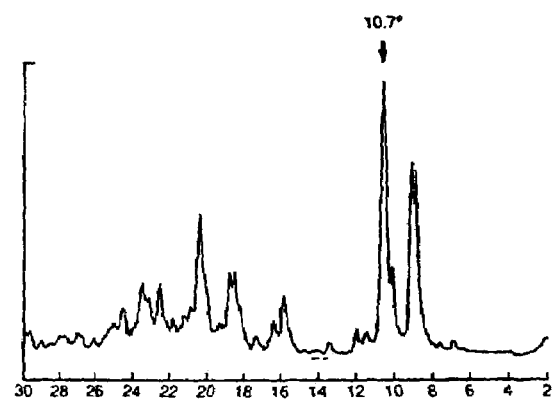
FIG. 1: X-ray diffractogram of powders of form II of torsemide as published by Kondo et al. in Iyakuhin Kenkyu Vol. 25 No. 9 (1994). On the Y axis is represented intensity, whilst the X axis reports the angle of reflection (in degrees 2 theta), decreasing from left to right.
Figure 2:
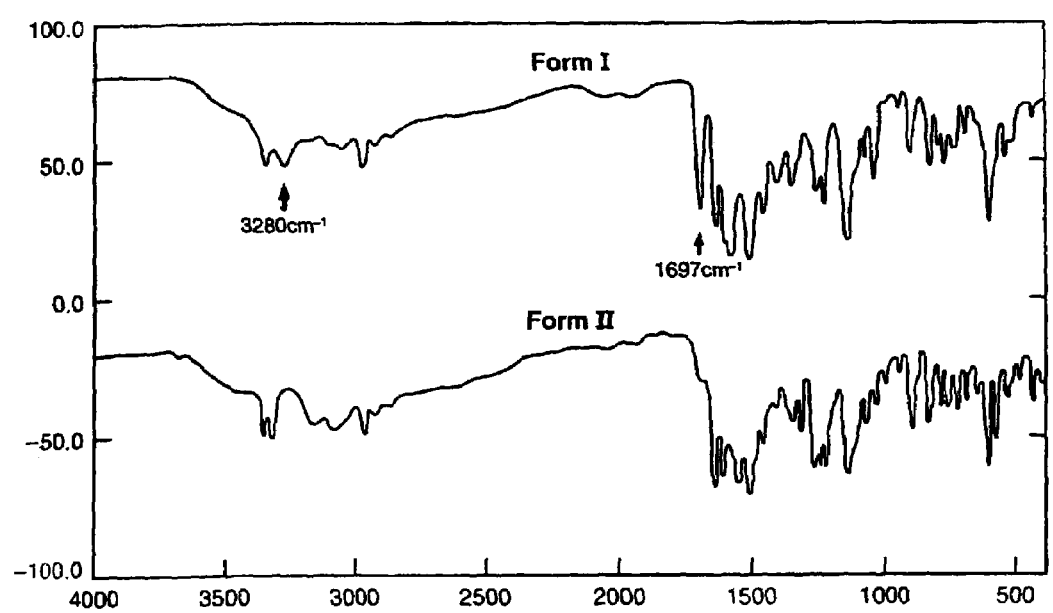
FIG. 2: FT-IR spectra of form II and form I of torsemide as published by Kondo et al. in Iyakuhin Kenkyu Vol. 25 No. 9 (1994). On the Y axis is represented the transmittance (in %), whilst the X axis reports the wave number (in $cm^{-1}$).

It has in fact been surprisingly found that—contrary to what taught by Kondo et al.—form II of torsemide (as previously characterised by Kondo through the X-ray diffractograms of the powders of FIG. 1 and through the FT-IR spectra of FIG. 2), and more preferably the pure and stable form II of torsemide obtainable through the procedure described in the present patent application, is quite stable under normal storage conditions (non anhydrous) in the treatment of products in the pharmaceutical industry and in the distribution of medicines to allow the preparation of solid pharmaceutical forms, in that—within the limits of detection—it does not undergo any transformation into form I of torsemide. Consequently, the present invention makes available, for the first time, solid pharmaceutical compositions comprising form II of torsemide as active ingredient.

Within the ambit of the present invention, "pure" form II of torsemide is intended as a form II of torsemide which according to the analysis of the FT-IR spectra registered in KBr contains less than 1% (by weight) of form I of torsemide.

Within the ambit of the present invention, "stable" form II of torsemide is intended as a pure form II which does not show detectable polymorphic transformations after 6 months of accelerated testing (at 40°±2° C./75±5% of relative humidity) as by the ICH (Q1A, "Stability testing of new Drug Substances and new Drug Products", $1^{st}$ edition Oct. 27, 1997 and $2^{nd}$ edition Nov. 8, 2000). For detectable polymorphic transformations is intended transformations visible from changes of the FT-IR spectrum of form II of torsemide registered in KBr. Specifically, the formation of a contamination of 1% or greater (by weight) of form I of torsemide in a sample of pure form II of torsemide would be a detectable polymorphic transformation by means of the relative change of the FT-IR spectrum registered in KBr which would imply the appearance of a peak in the position at 1697 $cm^{-1}$.

More precisely, pure and stable form II of torsemide is characterised through the following signals in the X-ray diffractogram of the powders expressing degrees 2 theta: 9.0±0.1; 9.2±0.1; 10.7±0.1; 15.9±0.1; 18.2±0.1; 18.5±0.1; 18.8±0.1; 20.4±0.1; 22.6±0.1; 23.1±0.1; 23.5±0.1. Still more precisely, pure and stable form II of torsemide is characterised through the additional peaks in the X-ray diffractogram reported in table 2. Still more precisely, pure and stable form II of torsemide is characterised through the X-ray diffractogram of the powders of FIG. 3. Still more precisely, pure and stable form II of torsemide is characterised through the following peaks in the FT-IR spectrum registered in KBr: 3354±2 $cm^{-1}$; 3326±2 $cm^{-1}$; 3085±2 $cm^{-1}$; 2964±2 $cm^{-1}$; 1617±2 $cm^{-1}$; 1555±2 $cm^{-1}$; 1510±2 $cm^{-1}$; 1357±2 $cm^{-1}$; 1326±2 $cm^{-1}$; 1277±2 $cm^{-1}$; 1234±2 $cm^{-1}$; 1151±2 $cm^{-1}$; 900±2 $cm^{-1}$; 837±2 $cm^{-1}$. Still more precisely, pure and stable form II of torsemide is characterised through the peaks in the FT-IR spectrum reported in table 4. Still more precisely, pure and stable form II of torsemide is characterised through the FT-IR spectra in KBr of FIG. 4 or 5.

Still more precisely, pure and stable form II of torsemide is characterised by a melting point in the interval between 159.9° C. and 160.2° C. (measured with a Büchi B-540 instrument).

As mentioned above, form II of torsemide the subject of the present invention is the form II of torsemide as characterised by Kondo et al. and consequently, it can be obtained through any procedure useful for the attainment of form II of torsemide (as characterised by Kondo et al.), naturally on the condition that the form II of torsemide thus obtained be pure and stable within the meaning of the present patent application (namely that the form II of torsemide effectively obtained does not contain detectable contaminations—greater than 1% by weight—of form I). With that aim, the procedure found by the inventors within the ambit of the present invention is particularly advantageous and preferred. In particular, pure and stable form II of torsemide is obtainable with high yield through the process perfected by the inventors of the present patent application and comprising the following steps:

suspension of crude, dried torsemide in 10 parts (by weight) of deionised water, the addition of a solution of 48% potassium hydrate, slowly with stirring, maintaining the temperature at 20–25° C., until achieving complete solution and without exceeding pH 12.5, filtration of the solution thus obtained through 40 micron paper filters, gradual acidification of the filtrate thus obtained with stirring with 80% acetic acid preferably until reaching a pH of 5.3–5.7 maintaining the temperature at 20–25° C. during the addition, obtaining a suspension, stirring of the suspension for 30 minutes at a temperature of 20–25° C., filtration by suction and washing the solid obtained with water, drying of the solid in a dryer under vacuum at a temperature of 50° C.

Within the ambit of the present invention, as crude torsemide, is intended any torsemide obtainable through any suitable procedure described in the literature, leaving aside its crystalline form.

As initially said, it has been unexpectedly found that pure and stable form II of torsemide, as obtainable for example through the procedure of the present invention, does not require storage under strictly anhydrous conditions.

Whilst it has been confirmed that pure and stable form II of torsemide transforms into form I if suspended in water and if then subjected to strong heating or if suspended in water and subjected to prolonged treatment, it has instead been found that the pure and stable form of torsemide is not susceptible to transformation into form I under standard storage conditions, even in the presence of considerable relative humidity (75%±5%), in particular under the conditions envisaged by the "ICH" international standard (Q1A, "Stability testing of new Drug Substances and new Drug Products", $1^{st}$ edition Oct. 27, 1997 and $2^{nd}$ edition Nov. 8, 2000) and recognised on the world scale for the evaluation of the stability of pharmaceutical substances.

It is thus found that the pure form II of torsemide as had already been described and characterised by Kondo et al. and preferably as obtainable through the methods of the present invention is not susceptible to humidity during usual storage conditions and consequently, form II of torsemide is indicated for the preparation of solid pharmaceutical formulations which could take advantage of greater solubility of form II (with respect to form I) of torsemide. Consequently, the present invention proposes, for the first time, solid pharmaceutical compositions comprising form II of 1-isopropyl-3-[(4-m-toluidino-3-pyridyl)sulphonyl]-urea as active ingredient.

EXPERIMENTAL SECTION

Example 1

Synthesis of Form II of Torsemide.

One of the chemical synthesis usable to obtain a preparation of crude torsemide is for example the chemical synthesis of torsemide used by Kondo at al., in particular according to FIG. 2 by Kondo. Torsemide thus obtained, following the elimination of the acetone, following the addition of water and following precipitation of the torsemide from the remaining aqueous phase through the addition of acetic acid (until reaching a pH of 5.5) and following washing with deionised water can be used as "crude" torsemide, as defined within the ambit of the present patent application. 49 g of crude, dried torsemide (m.w.=348.43, 0.140 mol) are resuspended in 490 cc of deionised water. Later, 16.5 g of 48% potassium hydrate (m.w.=56.1; 0.141 mol) is slowly added, maintaining the temperature at 20–25° C., until the attainment of complete solution and without exceeding pH 12.5 (pH 12.35 has been reached). The solution is then filtered through 40 micron filter paper.

One then proceeds to the acidification of the filtered solution, to pH 5.3–5.7, by the gradual addition of 11.5 g of 80% acetic acid (m.w.=60.05; 0.153 mol), maintaining the temperature at 20–25° C. during the addition. After having stirred the suspension for 30 minutes at a temperature of 20–25° C., it is filtered by suction, washing the product filter bed with water. The product thus obtainable is then dried in a dryer under vacuum at a temperature of 50° C., finally yielding 47 g of pure torsemide form II (yield, with respect to crude torsemide=96%).

The melting point of the pure form II of torsemide used by the inventors of the present patent application measured with a Büchi B-540 according to USP class 1a (temperature increments of 1° C.±0.5° C./min starting from 10° C. from the expected melting point, inserting the sample at 5° C. from the melting point, then 1° C.±0.5° C./min until reaching the melting point) is 159.9°–160.2° C.

Figure 3:
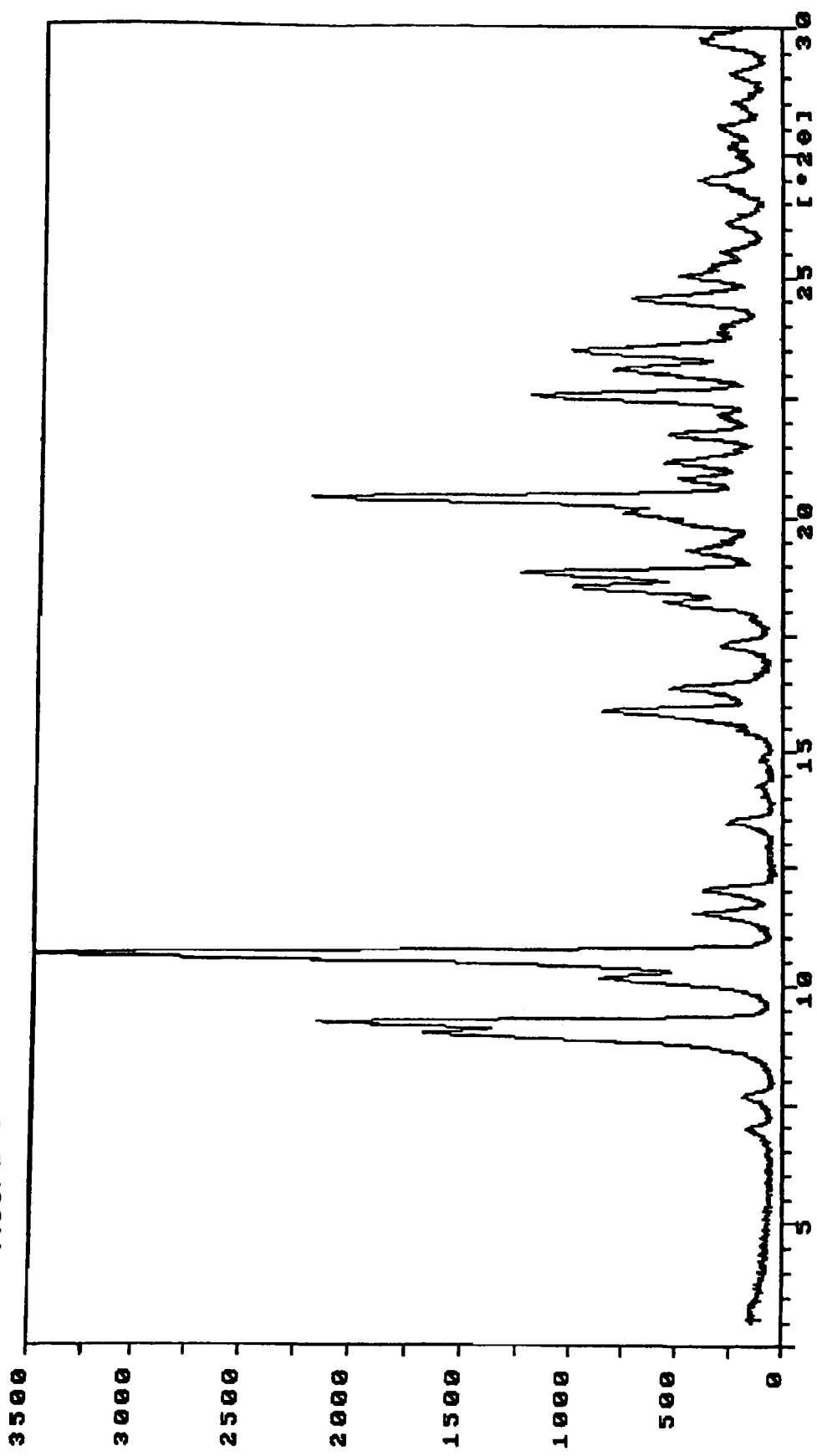
FIG. 3: X-ray diffractogram of powders of form II of torsemide as obtainable through the process of the present invention. On the Y axis is represented the intensity (counts), whilst the X axis reports the angle of reflection (in degrees 2 theta) increasing from left to right.

The X-ray diffractogram of the powders of form II of torsemide used by the inventors of the present patent application with a PW 1700 diffractometer (radiation source Cu α1 and α2 (λ=1.54051 Angstrom and λ=1.54430 Angstrom) is represented in FIG. 3.

The measurement conditions of the diffractogram of FIG. 3 are summarised in table 1, whilst the details of the diffractogram of FIG. 3 are reported in table 2:

TABLE 1

| Sample identification: | TORSEMIDE II |
| --- | --- |
| diffractometer type: | PW1710 BASED |
| Tube Anode: | Cu |
| Generator tension [kV]: | 40 |
| generator current [mA]: | 40 |
| Wavelength alpha1 [Å]: | 1.54051 |
| Wavelength alpha2 [Å]: | 1.54439 |
| Intensity ratio (alpha 2/alpha 1): | 0.500 |
| Divergence slit: | 1° |
| Receiving slit: | 0.1 |
| Monochromator used: | YES |
| Start angle [°2θ]: | 3.000 |
| End angle [°2θ]: | 30.000 |
| Step size [°2θ]: | 0.010 |
| Maximum intensity: | 3433.960 |
| Time per step [s]: | 0.7000 |
| Type of scan: | STEP |
| Minimum peak tip width: | 0.00 |
| Maximum peak tip width: | 1.00 |
| Peak base width: | 2.00 |
| Minimum significance: | 0.75 |
| Number of peaks: | 46 |

TABLE 2

| Angle [° 2θ] | Value d α1 [Å] | Value d α2 [Å] | Peak width [° 2θ] | Peak intensity [counts] | Base intensity [counts] | Relative intensity [%] | Significance |
| --- | --- | --- | --- | --- | --- | --- | --- |
| 3.300 | 26.7506 | 26.8180 | 0.160 | 71 | 71 | 2.1 | 0.77 |
| 6.990 | 12.6351 | 12.6669 | 0.160 | 88 | 58 | 2.6 | 5.24 |

TABLE 2-continued

| Angle [° 2θ] | Value d α1 [Å] | Value d α2 [Å] | Peak width [° 2θ] | Peak intensity [counts] | Base intensity [counts] | Relative intensity [%] | Significance |
|---|---|---|---|---|---|---|---|
| 7.680 | 11.5014 | 11.5304 | 0.160 | 121 | 58 | 3.5 | 7.04 |
| 8.995 | 9.8227 | 9.8475 | 0.030 | 1632 | 58 | 47.5 | 0.77 |
| 9.210 | 9.5939 | 9.6181 | 0.060 | 2116 | 58 | 61.6 | 3.29 |
| 9.265 | 9.5371 | 9.5611 | 0.040 | 1673 | 58 | 48.7 | 0.83 |
| 10.170 | 8.6903 | 8.7122 | 0.180 | 773 | 58 | 22.5 | 13.17 |
| 10.645 | 8.3036 | 8.3245 | 0.170 | 3434 | 58 | 100.0 | 53.08 |
| 11.530 | 7.6682 | 7.6875 | 0.060 | 361 | 58 | 10.5 | 1.81 |
| 12.060 | 7.3323 | 7.3508 | 0.060 | 266 | 58 | 7.7 | 1.34 |
| 13.485 | 6.5605 | 6.5771 | 0.160 | 190 | 58 | 5.5 | 8.88 |
| 14.255 | 6.2078 | 6.2235 | 0.120 | 48 | 58 | 1.4 | 1.41 |
| 14.845 | 5.9624 | 5.9774 | 0.160 | 34 | 58 | 1.0 | 1.52 |
| 15.420 | 5.7414 | 5.7558 | 0.100 | 119 | 58 | 3.5 | 1.10 |
| 15.870 | 5.5796 | 5.5936 | 0.050 | 795 | 58 | 23.2 | 0.80 |
| 15.925 | 5.5604 | 5.5744 | 0.060 | 686 | 58 | 20.0 | 1.56 |
| 16.375 | 5.4086 | 5.4222 | 0.080 | 449 | 58 | 13.1 | 2.57 |
| 17.300 | 5.1214 | 5.1343 | 0.180 | 231 | 58 | 6.7 | 9.53 |
| 18.200 | 4.8702 | 4.8824 | 0.160 | 471 | 58 | 13.7 | 8.78 |
| 18.530 | 4.7842 | 4.7962 | 0.080 | 936 | 58 | 27.3 | 3.45 |
| 18.840 | 4.7061 | 4.7180 | 0.080 | 1156 | 58 | 33.7 | 3.84 |
| 19.325 | 4.5891 | 4.6007 | 0.160 | 380 | 58 | 11.1 | 6.64 |
| 19.875 | 4.4633 | 4.4746 | 0.100 | 376 | 58 | 11.0 | 1.25 |
| 20.125 | 4.4085 | 4.4196 | 0.100 | 686 | 58 | 20.0 | 2.08 |
| 20.410 | 4.3475 | 4.3585 | 0.060 | 2116 | 58 | 61.6 | 2.51 |
| 20.465 | 4.3360 | 4.3469 | 0.030 | 1764 | 58 | 51.4 | 0.94 |
| 20.855 | 4.2558 | 4.2665 | 0.030 | 441 | 58 | 12.8 | 1.24 |
| 21.195 | 4.1883 | 4.1988 | 0.140 | 493 | 58 | 14.4 | 7.08 |
| 21.765 | 4.0798 | 4.0901 | 0.140 | 480 | 58 | 14.0 | 8.57 |
| 22.155 | 4.0089 | 4.0190 | 0.140 | 240 | 58 | 7.0 | 3.12 |
| 22.555 | 3.9387 | 3.9486 | 0.070 | 1129 | 58 | 32.9 | 2.93 |
| 23.105 | 3.8462 | 3.8559 | 0.200 | 734 | 58 | 21.4 | 12.91 |
| 23.475 | 3.7864 | 3.7959 | 0.180 | 936 | 58 | 27.3 | 18.52 |
| 24.055 | 3.6964 | 3.7057 | 0.100 | 202 | 58 | 5.9 | 0.86 |
| 24.560 | 3.6215 | 3.6306 | 0.070 | 655 | 58 | 19.1 | 2.14 |
| 25.020 | 3.5560 | 3.5649 | 0.120 | 404 | 58 | 11.8 | 4.08 |
| 25.225 | 3.5275 | 3.5364 | 0.120 | 279 | 58 | 8.1 | 1.21 |
| 25.525 | 3.4867 | 3.4955 | 0.180 | 213 | 58 | 6.2 | 5.49 |
| 26.125 | 3.4080 | 3.4166 | 0.160 | 219 | 58 | 6.4 | 5.46 |
| 26.985 | 3.3013 | 3.3096 | 0.160 | 350 | 58 | 10.2 | 6.50 |
| 27.495 | 3.2412 | 3.2494 | 0.100 | 146 | 58 | 4.3 | 0.76 |
| 27.630 | 3.2257 | 3.2338 | 0.060 | 213 | 58 | 6.2 | 1.24 |
| 28.035 | 3.1800 | 3.1880 | 0.220 | 243 | 58 | 7.1 | 10.23 |
| 28.530 | 3.1259 | 3.1338 | 0.070 | 156 | 58 | 4.6 | 1.49 |
| 29.090 | 3.0670 | 3.0748 | 0.180 | 193 | 58 | 5.6 | 7.62 |
| 29.720 | 3.0034 | 3.0110 | 0.160 | 313 | 58 | 9.1 | 4.63 |

Figure 4:
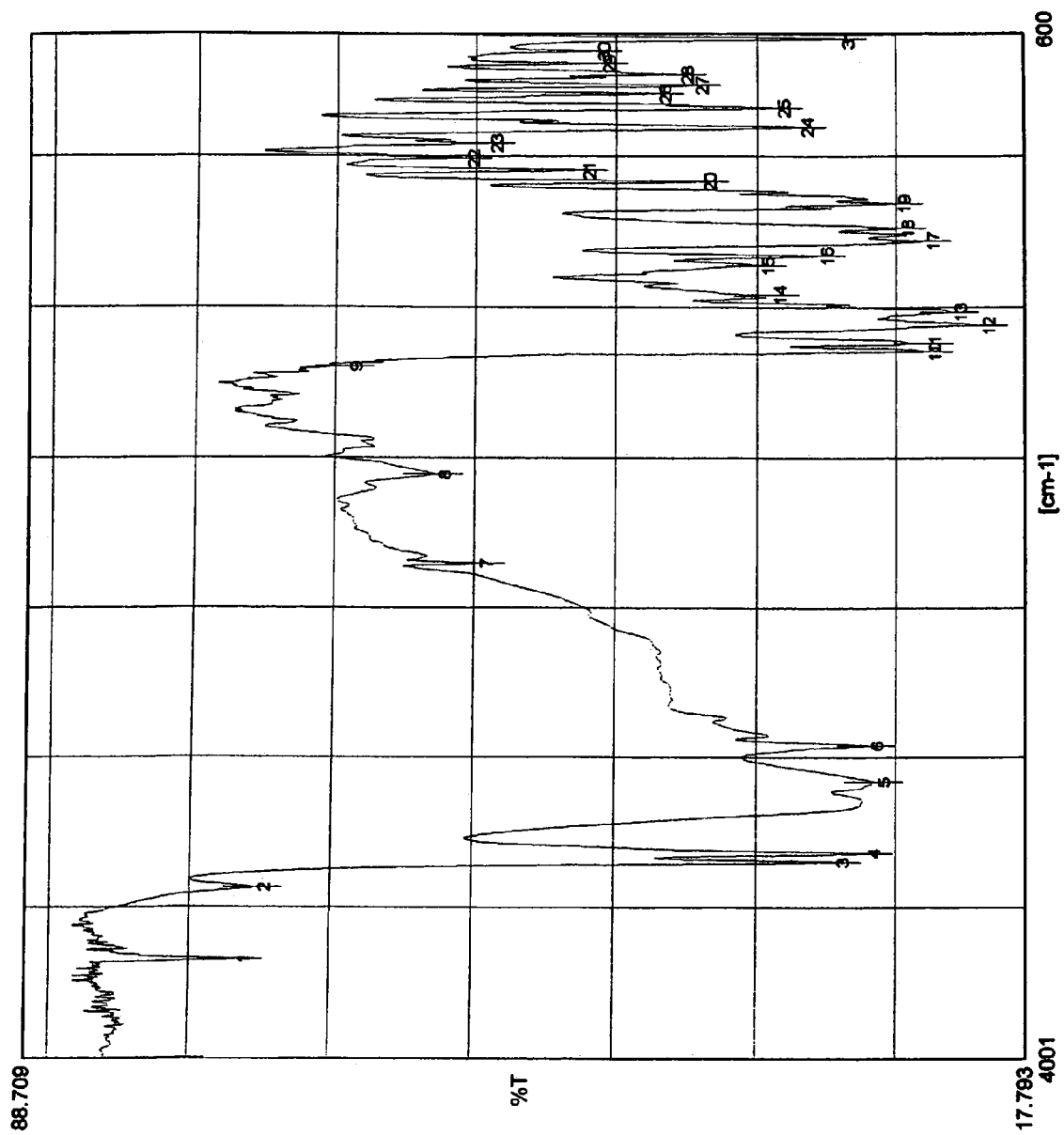
FIG. 4: FT-IR spectrum (Jasco) of form II of torsemide as obtainable by the process of the present invention. On the Y axis is represented the transmittance (in %), whilst the X axis reports the wave number (in $cm^{-1}$).

FT-IR spectrum, registered in KBr with a Jasco FT-IR 300-E ("diffuse reflectance") of form II of torsemide used by the inventors of the present patent application is represented in FIG. 4.

The measurement conditions of the FT-IR spectrum of FIG. 4 are summarised in table 3, whilst some details of the spectrum are summarised in table 4.

TABLE 3

| Accumulation | 32 times |
|---|---|
| Resolution | 4 cm$^{-1}$ |
| Apodisation | Cosine |
| Sample name | Torsemide II |
| Gain | 16 |
| Speed | 2.0 mm/sec |
| Delay time | 0 sec |
| Light source | Ni/Cr Filament |
| Detector | 1 |
| Beam splitter | KBr |

TABLE 4

| Peak number | Peak position [cm$^{-1}$] | Transmittance |
|---|---|---|
| 1 | 3678.55 | 73.9% |
| 2 | 3440.38 | 72.6% |
| 3 | 3354.57 | 31.5% |
| 4 | 3325.64 | 29.2% |
| 5 | 3085.55 | 28.5% |
| 6 | 2964.05 | 29.0% |
| 7 | 2352.73 | 56.9% |
| 8 | 2053.82 | 60.0% |
| 9 | 1694.16 | 66.4% |
| 10 | 1643.05 | 24.9% |
| 11 | 1616.06 | 24.9% |
| 12 | 1555.31 | 21.0% |
| 13 | 1511.23 | 23.0% |
| 14 | 1455.03 | 36.0% |
| 15 | 1356.68 | 36.9% |
| 16 | 1325.82 | 32.7% |
| 17 | 1276.65 | 25.0% |
| 18 | 1234.22 | 26.8% |
| 19 | 1151.29 | 27.1% |
| 20 | 1078.98 | 41.0% |
| 21 | 1041.37 | 49.7% |
| 22 | 1001.84 | 58.0% |

TABLE 4-continued

| Peak number | Peak position [cm⁻¹] | Transmittance |
|---|---|---|
| 23 | 952.66 | 56.3% |
| 24 | 899.63 | 34.1% |
| 25 | 836.95 | 35.8% |
| 26 | 789.71 | 44.2% |
| 27 | 763.67 | 41.6% |
| 28 | 727.03 | 42.6% |
| 29 | 691.36 | 48.3% |
| 30 | 650.86 | 48.7% |
| 31 | 609.40 | 31.1% |

Figure 5:
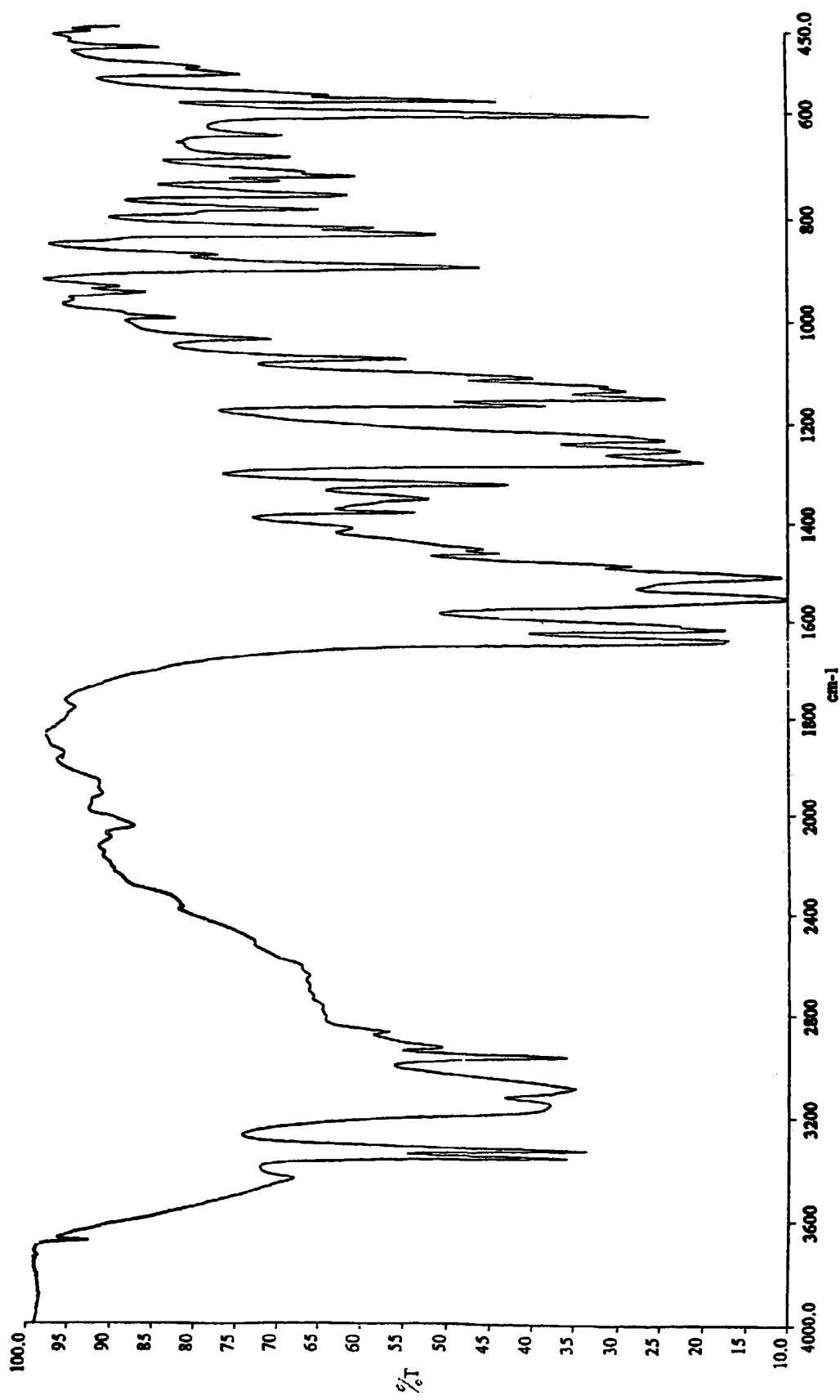
FIG. 5: FT-IR spectrum (Perkin Elmer) of form II of torsemide as obtainable through the procedure of the present invention. On the Y axis is represented the transmittance (in %), whilst the X axis reports the wave number (in $cm^{-1}$).
Figure 6:
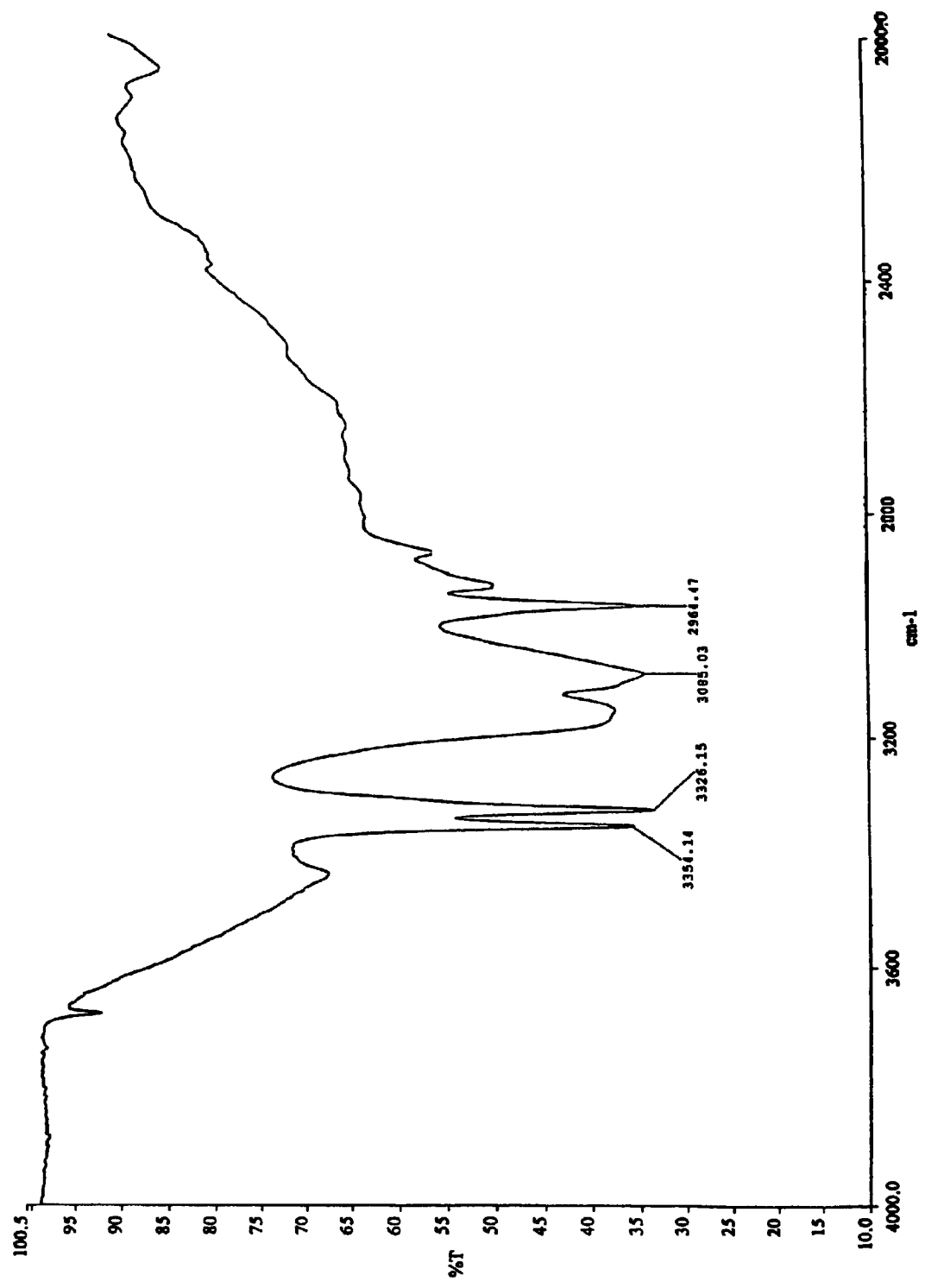
FIG. 6: Enlargement (4000–2000 $cm^{-1}$) of the FT-IR spectrum (Perkin Elmer) of form II of torsemide as obtainable trough the procedure of the present invention. On the Y axis is represented the transmittance (in %), whilst the X axis reports the wave number (in $cm^{-1}$).
Figure 7:
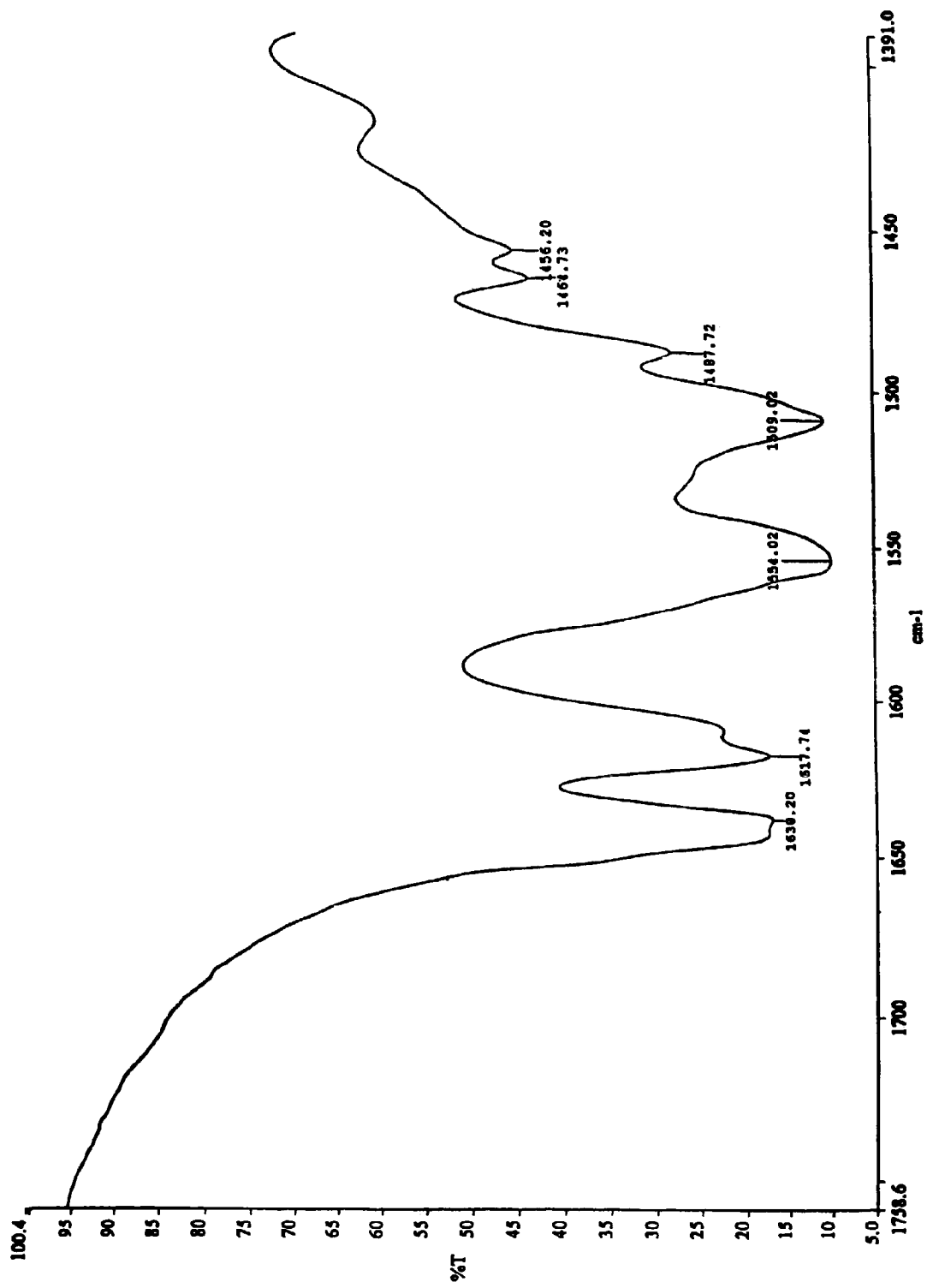
FIG. 7: Enlargement (1758.6–1391.0 $cm^{-1}$) of the FT-IR spectrum (Perkin Elmer) of form II of torsemide as obtainable through the procedure of the present invention. On the Y axis is represented the transmittance (in %), whilst the X axis reports the wave number (in $cm^{-1}$).
Figure 8:
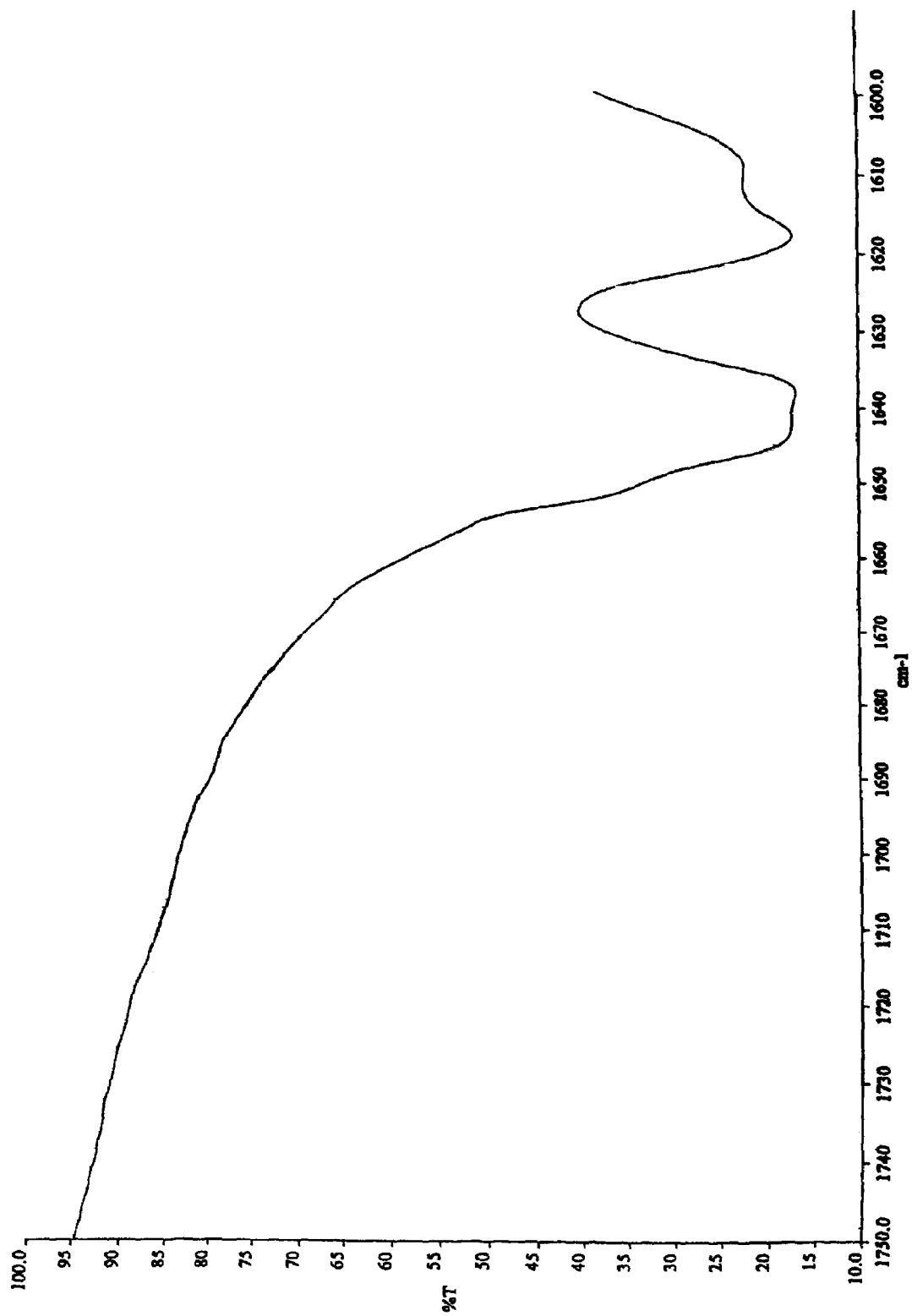
FIG. 8: Enlargement (1750–1600 $cm^{-1}$) of the FT-IR spectrum (Perkin Elmer) of form II of torsemide as obtainable through the procedure of the present invention. On the Y axis is represented the transmittance (in %), whilst the X axis reports the wave number (in $cm^{-1}$).
Figure 9:
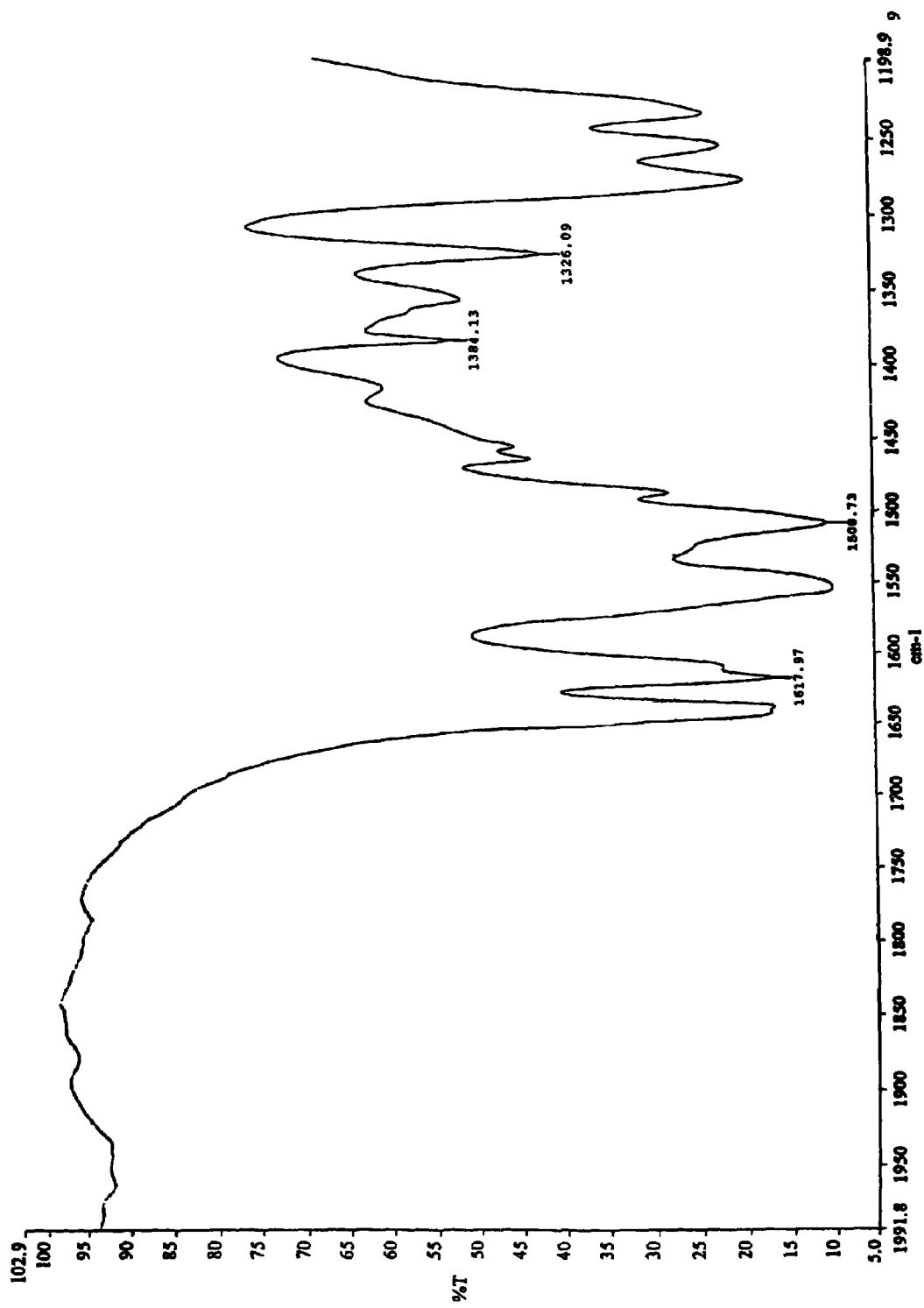
FIG. 9: Enlargement (1991.8–1198.9 $cm^{-1}$) of the FT-IR spectrum (Perkin Elmer) of form II of torsemide as obtainable through the procedure of the present invention. On the Y axis is represented the transmittance (in %), whilst the X axis reports the wave number (in $cm^{-1}$).
Figure 10:
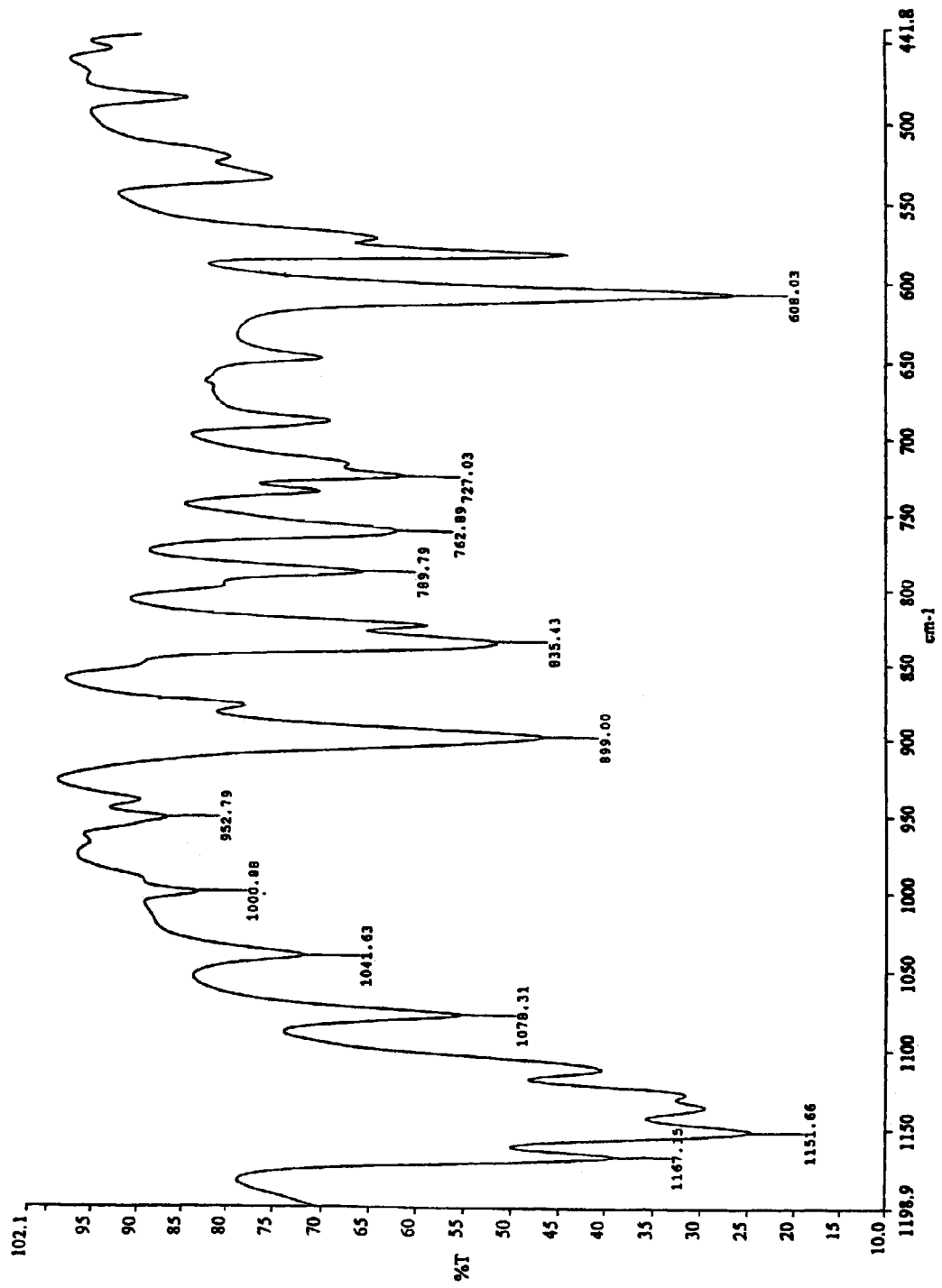
FIG. 10: Enlargement (1198.9–441.8 $cm^{-1}$) of the FT-IR spectrum (Perkin Elmer) of form II of torsemide as obtainable through the procedure of the present invention. On the Y axis is represented the transmittance (in %), whilst the X axis reports the wave number (in $cm^{-1}$).

The FT-IR spectrum, registered in KBr with a Perkin Elmer FT-IR Spectrum-one ("diffuse reflectance") of form II of torsemide used by the inventors of the present patent application is represented in FIG. 5. Various enlargements obtained with the Perkin Elmer FT-IR Spectrum-one with which some details of the FT-IR spectrum of torsemide form II used by the inventors of the present invention are better are represented in FIGS. 6–10.

Example 2

Synthesis of Form I of Torsemide.

Form I of torsemide is obtainable from form II of torsemide as above according to the instructions of Kondo, namely by suspension of an aliquot of form II in water (approx. 23 parts by weight) and subsequent stirring for 20 days at room temperature. The melting point of form I of torsemide, used by the inventors of the present patent application, measured with a Büchi B-540 according to USP class 1a (temperature increments of 1° C.±0.5° C./min starting from 10° C. from the expected melting point, inserting the sample at 5° C. from the melting point, then 1° C.±0.5° C./min until reaching the melting point), is 160.1°–160.5° C.

Figure 12:
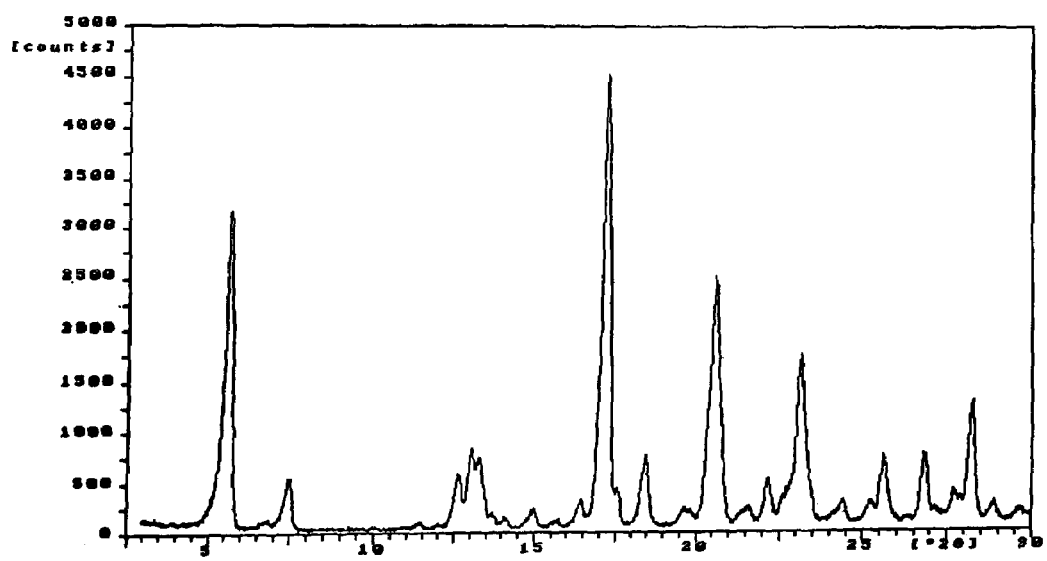
FIG. 12: X-ray diffractogram of powders of form I of torsemide used by the inventors of the present patent application. On the Y axis is represented the intensity (counts), whilst the X axis reports the angle of reflection (in degrees 2 theta) increasing from left to right.

The X-ray diffractogram of the torsemide form I used by the inventors of the present patent application with a PW 1700 diffractometer (radiation source Cu α1 and α2 (λ=1.54051 Angstrom and λ=1.54430 Angstrom) is represented in FIG. 12.

Figure 16:
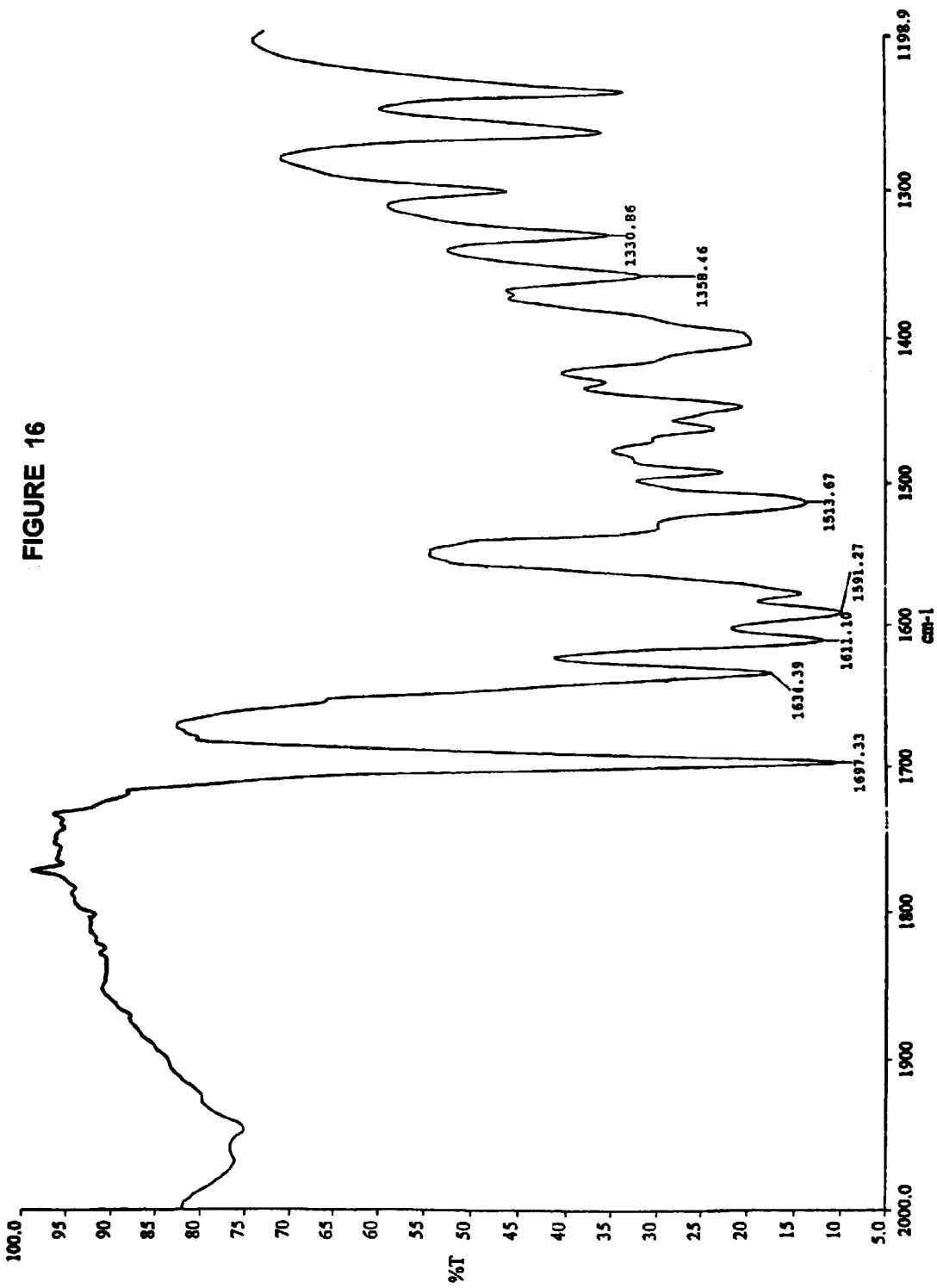
FIG. 16: Enlargement (2000–1198.9 $cm^{-1}$) of the FT-IR spectrum (Perkin Elmer) of form I of torsemide used by the inventors of the present patent application. On the Y axis is represented the transmittance (in %), whilst the X axis reports the wave number (in cm$^{-1}$).

The measurement conditions of the diffractogram of FIG. 12 are summarised in table 5, whilst the details of the diffractogram of FIG. 16 are reported in table 6:

TABLE 5

| | |
|---|---|
| Sample Identification: | TORSEMIDE I |
| diffractometer type: | PW1710 BASED |
| Tube Anode: | Cu |
| generator tension [kV]: | 40 |
| generator current [mA]: | 40 |
| Wavelength alpha1 [Å]: | 1.54051 |
| Wavelength alpha2 [Å]: | 1.54439 |
| Intensity ratio (alpha2/alpha1): | 0.500 |
| Divergence slit: | 1° |
| Receiving slit: | 0.1 |
| Monochromator used: | YES |
| Start angle [°2θ]: | 3.000 |
| End angle [°2θ]: | 30.000 |
| Step size [°2θ]: | 0.010 |
| Maximum intensity: | 4435.560 |
| Step time per step [s]: | 0.7000 |
| Scanning type of scan: | STEP |
| Minimum peak tip width: | 0.00 |
| Maximum peak tip width: | 1.00 |
| Peak base width: | 2.00 |
| Minimum significance: | 0.75 |
| Number of peaks: | 39 |

TABLE 6

| Angle [° 2θ] | Value d α1 [Å] | Value d α2 [Å] | Peak width [° 2θ] | Peak intensity [counts] | Base intensity [counts] | Relative intensity [%] | Significance |
|---|---|---|---|---|---|---|---|
| 3.080 | 28.6608 | 28.7330 | 0.320 | 96 | 41 | 2.2 | 0.76 |
| 3.900 | 22.6363 | 22.6934 | 0.070 | 69 | 41 | 1.6 | 0.91 |
| 5.650 | 15.6284 | 15.6678 | 0.130 | 3058 | 41 | 68.9 | 33.82 |
| 6.840 | 12.9119 | 12.9444 | 0.140 | 79 | 41 | 1.8 | 1.78 |
| 7.505 | 11.7692 | 11.7988 | 0.070 | 506 | 41 | 11.4 | 2.32 |
| 10.080 | 8.7677 | 8.7898 | 0.160 | 17 | 41 | 0.4 | 1.03 |
| 11.415 | 7.7451 | 7.7647 | 0.200 | 62 | 41 | 1.4 | 3.10 |
| 12.025 | 7.3536 | 7.3721 | 0.120 | 40 | 41 | 0.9 | 1.39 |
| 12.695 | 6.9670 | 6.9845 | 0.070 | 520 | 41 | 11.7 | 1.90 |
| 13.060 | 6.7731 | 6.7901 | 0.160 | 762 | 41 | 17.2 | 8.30 |
| 13.310 | 6.6464 | 6.6631 | 0.030 | 681 | 41 | 15.4 | 0.76 |
| 13.470 | 6.55678 | 6.5843 | 0.080 | 357 | 41 | 8.1 | 0.77 |
| 13.710 | 6.4534 | 6.4696 | 0.120 | 144 | 41 | 3.2 | 1.06 |
| 14.105 | 6.2735 | 6.2893 | 0.100 | 100 | 41 | 2.3 | 1.33 |
| 15.010 | 5.8972 | 5.9121 | 0.100 | 190 | 41 | 4.3 | 2.00 |
| 15.720 | 5.6325 | 5.6466 | 0.080 | 81 | 41 | 1.8 | 0.88 |
| 16.440 | 5.3874 | 5.4009 | 0.140 | 243 | 41 | 5.5 | 3.98 |
| 17.240 | 5.1391 | 5.1521 | 0.120 | 4436 | 41 | 100.0 | 22.70 |
| 17.645 | 5.0221 | 5.0347 | 0.070 | 306 | 41 | 6.9 | 1.39 |
| 18.465 | 4.8009 | 4.8130 | 0.260 | 692 | 41 | 15.6 | 32.51 |
| 19.670 | 4.5094 | 4.5207 | 0.160 | 182 | 41 | 4.1 | 2.25 |
| 19.880 | 4.4622 | 4.4735 | 0.080 | 159 | 41 | 3.6 | 0.97 |
| 20.340 | 4.3623 | 4.3733 | 0.120 | 986 | 41 | 22.2 | 1.10 |
| 20.645 | 4.2986 | 4.3094 | 0.040 | 2162 | 41 | 48.7 | 0.99 |
| 20.820 | 4.2628 | 4.2736 | 0.080 | 858 | 41 | 19.4 | 1.42 |
| 21.595 | 4.1116 | 4.1219 | 0.100 | 210 | 41 | 4.7 | 1.49 |
| 22.110 | 4.0170 | 4.0271 | 0.060 | 365 | 41 | 8.2 | 1.34 |
| 22.210 | 3.9991 | 4.0092 | 0.100 | 471 | 41 | 10.6 | 3.13 |
| 22.600 | 3.9310 | 3.9409 | 0.080 | 296 | 41 | 6.7 | 0.76 |

TABLE 6-continued

| Angle [° 2θ] | Value d α1 [Å] | Value d α2 [Å] | Peak width [° 2θ] | Peak intensity [counts] | Base intensity [counts] | Relative intensity [%] | Significance |
|---|---|---|---|---|---|---|---|
| 23.150 | 3.8388 | 3.8485 | 0.050 | 1722 | 41 | 38.8 | 0.99 |
| 24.405 | 3.6442 | 3.6533 | 0.160 | 266 | 41 | 6.0 | 6.05 |
| 25.235 | 3.5261 | 3.5350 | 0.100 | 240 | 41 | 5.4 | 1.20 |
| 25.665 | 3.4680 | 3.4768 | 0.060 | 681 | 41 | 15.4 | 1.62 |
| 26.355 | 3.3788 | 3.3873 | 0.120 | 98 | 41 | 2.2 | 1.24 |
| 26.770 | 3.3273 | 3.3357 | 0.050 | 600 | 41 | 13.5 | 0.79 |
| 27.725 | 3.2149 | 3.2229 | 0.120 | 346 | 41 | 7.8 | 2.80 |
| 28.235 | 3.1579 | 3.1659 | 0.050 | 1218 | 41 | 27.5 | 1.30 |
| 28.890 | 3.0878 | 3.0956 | 0.180 | 228 | 41 | 5.1 | 6.10 |
| 29.595 | 3.0158 | 3.0234 | 0.160 | 161 | 41 | 3.6 | 2.95 |

Figure 13:
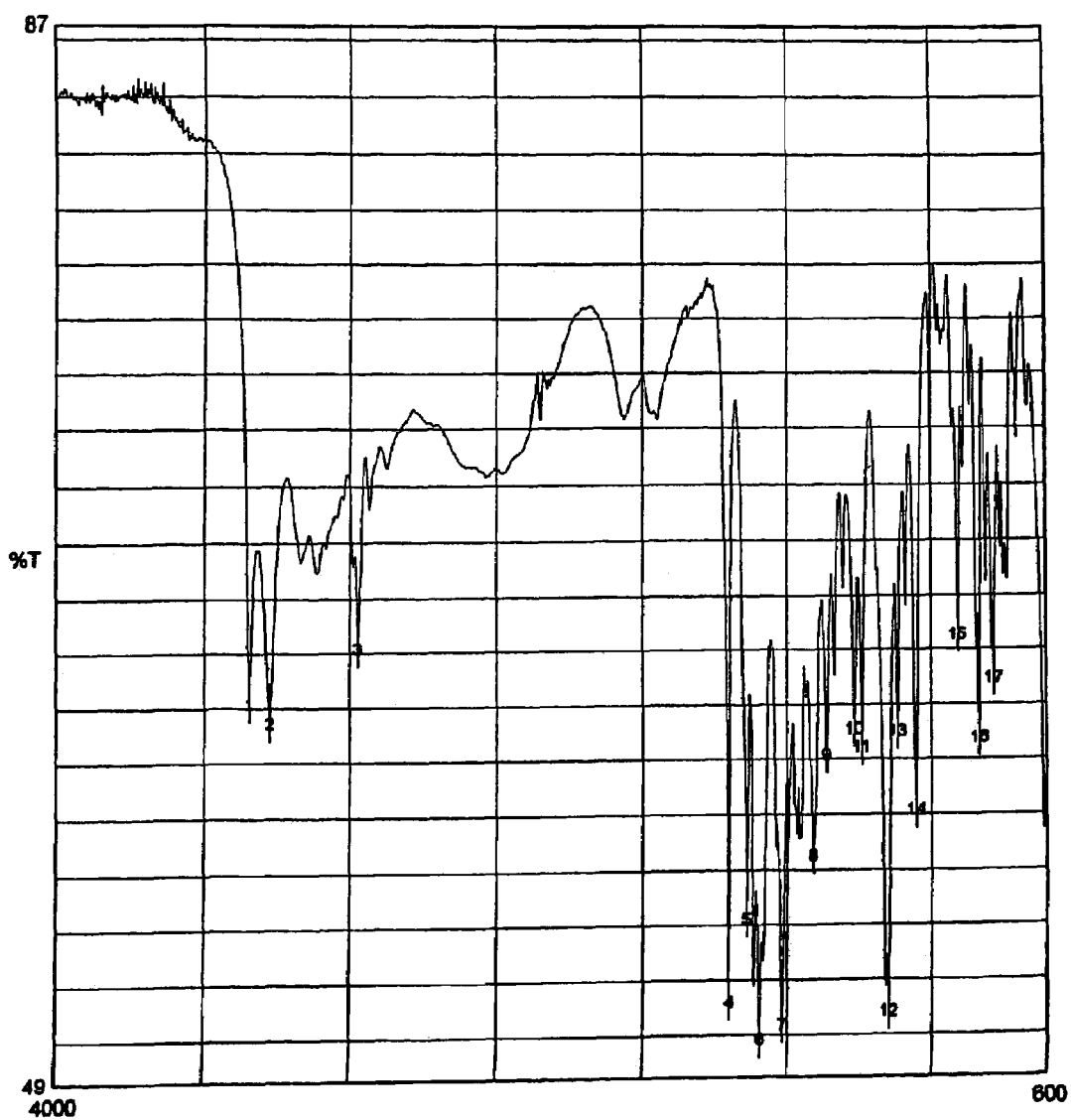
FIG. 13: FT-IR spectrum (Jasco) of form I of torsemide used by the inventors of the present patent application. On the Y axis is represented the transmittance (in %), whilst the X axis reports the wave number (in $cm^{-1}$).

The FT-IR spectrum, registered in KBr with a Jasco FT-IR 300-E ("diffuse reflectance") of form I torsemide used by the inventors of the present patent application is represented in FIG. 13.

The measurement conditions of the FT-IR spectrum of FIG. 13 are summarised in table 7, whilst the details of the spectrum are summarised in table 8.

TABLE 7

| Accumulation | 32 times |
|---|---|
| Resolution | 4 cm$^{-1}$ |
| Apodisation | Cosine |
| Sample name | Torsemide I |
| Gain | 16 |
| Speed | 2.0 mm/sec |
| Delay time | 0 sec |
| Light source | Ni/Cr Filament |
| Detector | 1 |
| Beam splitter | KBr |

TABLE 8

| Peak number | Peak position | Transmittance |
|---|---|---|
| 1 | 3350.71 | 63.6% |
| 2 | 3280.32 | 62.8% |
| 3 | 2976.59 | 65.5% |
| 4 | 1697.05 | 52.5% |
| 5 | 1633.41 | 55.5% |
| 6 | 1590.99 | 51.2% |
| 7 | 1515.77 | 51.7% |
| 8 | 1403.92 | 57.9% |
| 9 | 1359.57 | 61.5% |
| 10 | 1263.15 | 62.5% |
| 11 | 1237.11 | 61.8% |
| 12 | 11.43.58 | 52.2% |
| 13 | 1110.80 | 62.4% |
| 14 | 1047.16 | 59.6% |
| 15 | 900.59 | 65.9% |
| 16 | 823.46 | 62.2% |
| 17 | 774.28 | 64.3% |

Figure 14:
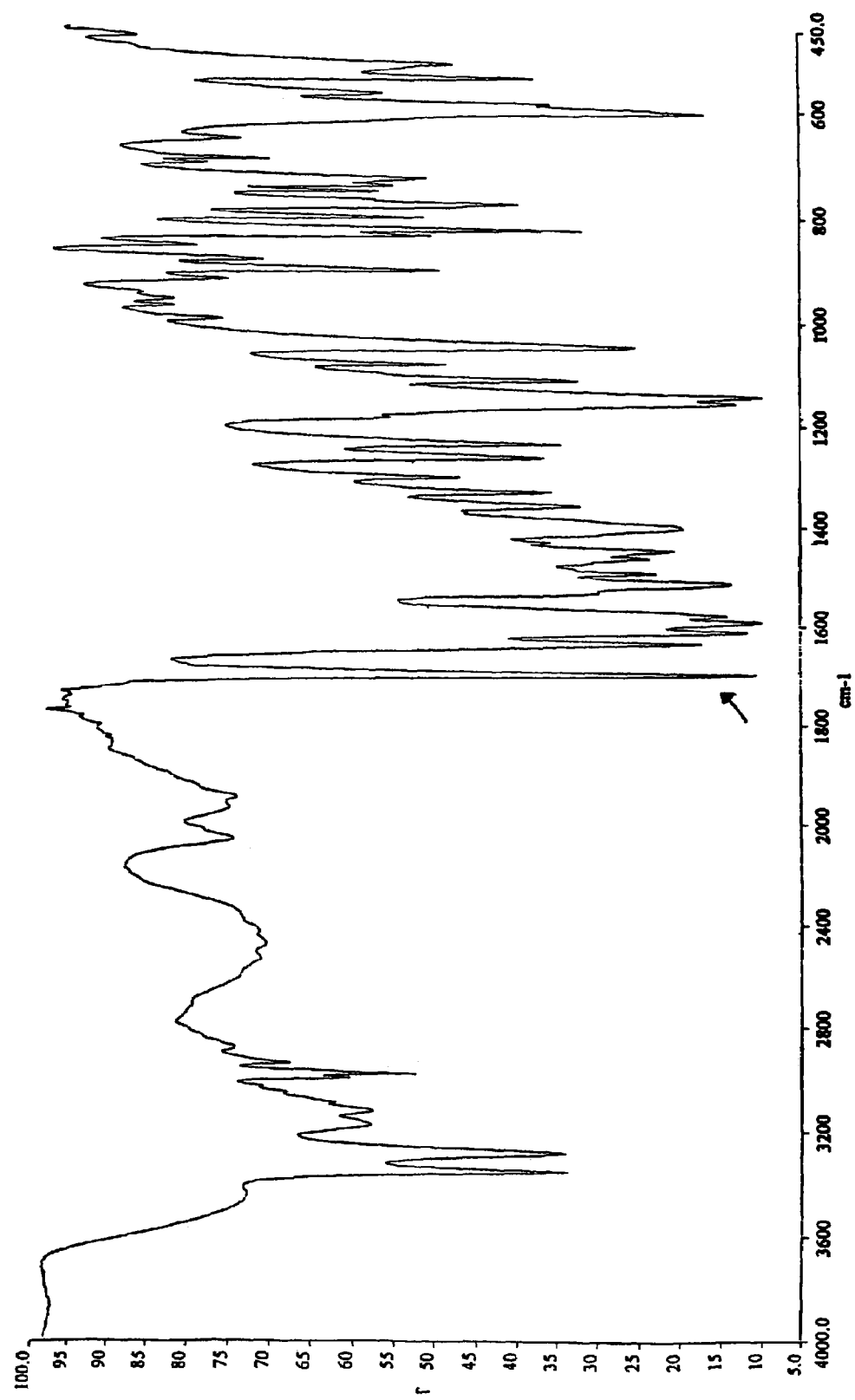
FIG. 14: FT-IR spectrum (Perkin Elmer) of form I of torsemide used by the inventors of the present patent application. On the Y axis is represented the transmittance (in %), whilst the X axis reports the wave number (in $cm^{-1}$).
Figure 15:
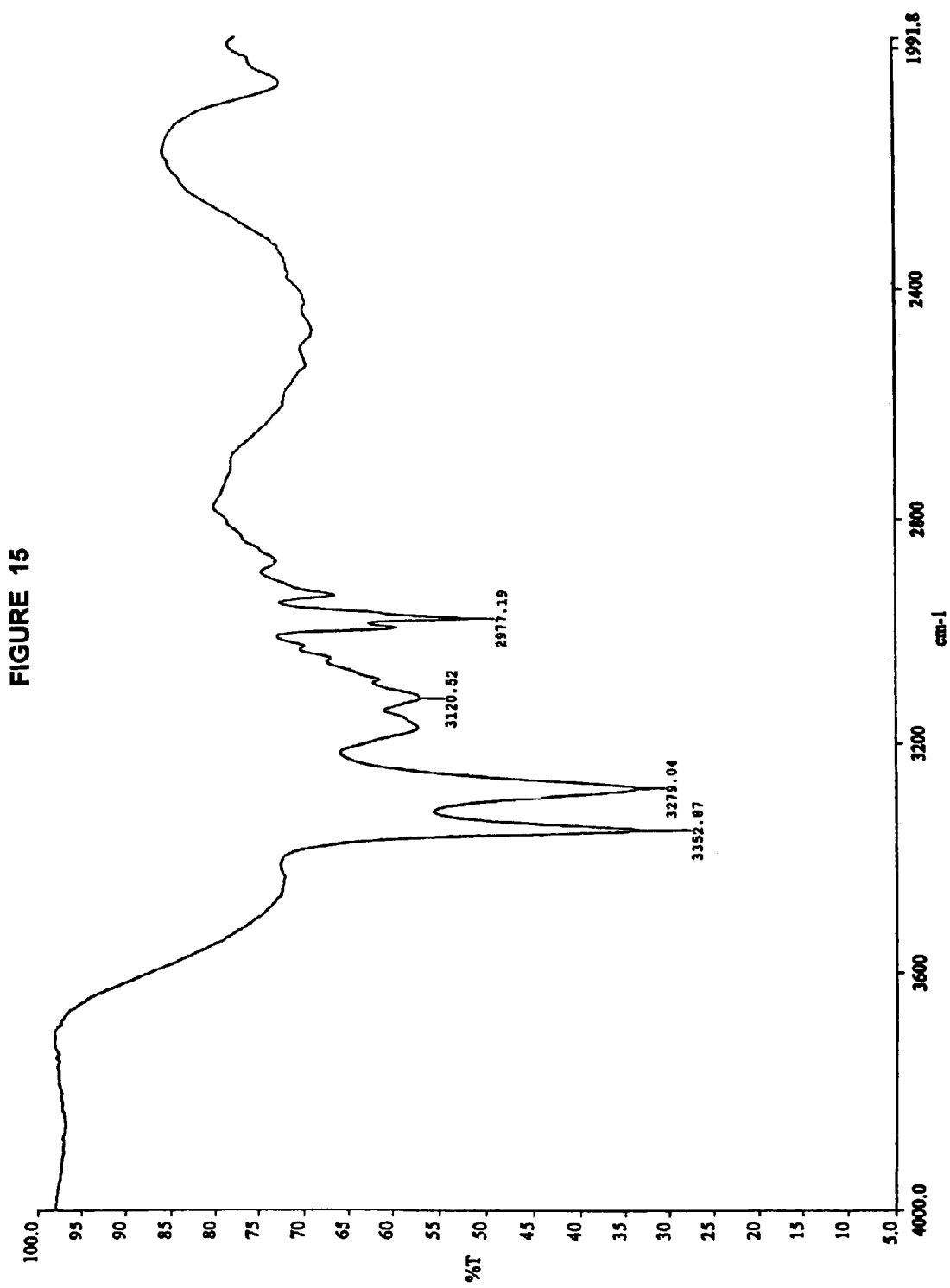
FIG. 15: Enlargement (4000–1991.8 $cm^{-1}$) of the FT-IR spectrum (Perkin Elmer) of form I of torsemide used by the inventors of the present patent application. On the Y axis is represented the transmittance (in %), whilst the X axis reports the wave number (in $cm^{-1}$).
Figure 17:
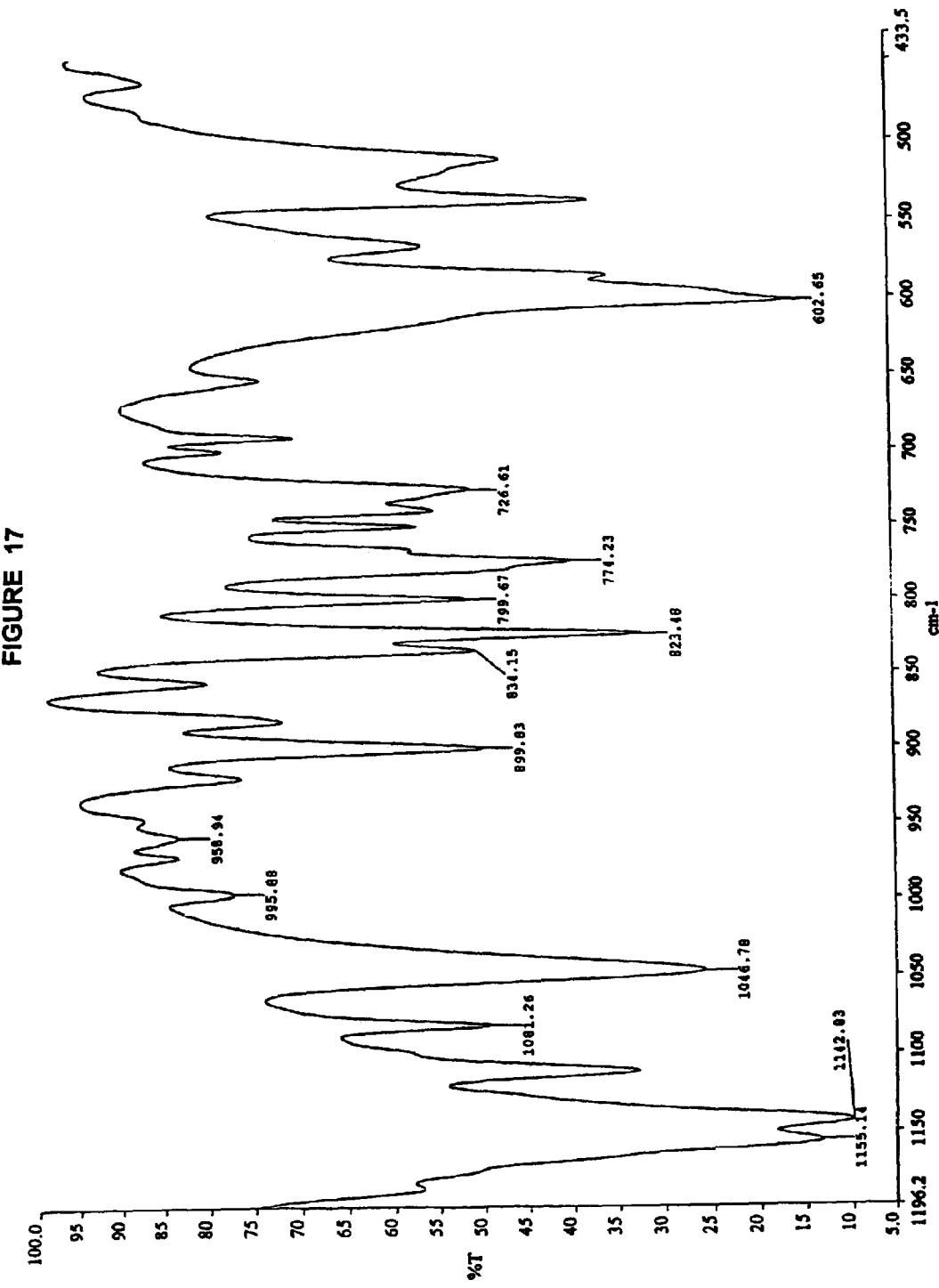
FIG. 17: Enlargement (1196.2–433.5 cm$^{-1}$) of the FT-IR spectrum (Perkin Elmer) of form I of torsemide used by the inventors of the present patent application. On the Y is represented the transmittance (in %), whilst the X axis reports the wave number (in cm$^{-1}$).

The IR spectrum, registered in KBr with a Perkin Elmer FT-IR Spectrum-one ("diffuse reflectance") of form I of torsemide used by the inventors of the present patent application is represented in FIG. 14. Various enlargements obtained with the Perkin Elmer FT-IR Spectrum-one from which some details of the FT-IR spectrum of form I of torsemide used by the inventors of the present patent application are better, are represented in FIGS. 15–17.

Example 3

The Detection Limits of Contaminations of Form I in Samples of Form II of Torsemide.

To establish the most relevant and suitable analytical method for the detection of small quantities of contaminating form I of torsemide in a sample of form II of torsemide, the inventors have added defined quantities of form I to samples of pure form II and have registered the X-ray diffractograms of the powders as well as the FT-IR spectra in KBr of the mixtures thus obtained.

Example 3a

In this example, there have been added, respectively, 2%, 4% and 8% by weight of form I of torsemide to a sample of pure form II of torsemide. The X-ray diffractogram of the powders of the sample of form II of torsemide contaminated with 2% of form I is represented in FIG. 18.

Figure 18:
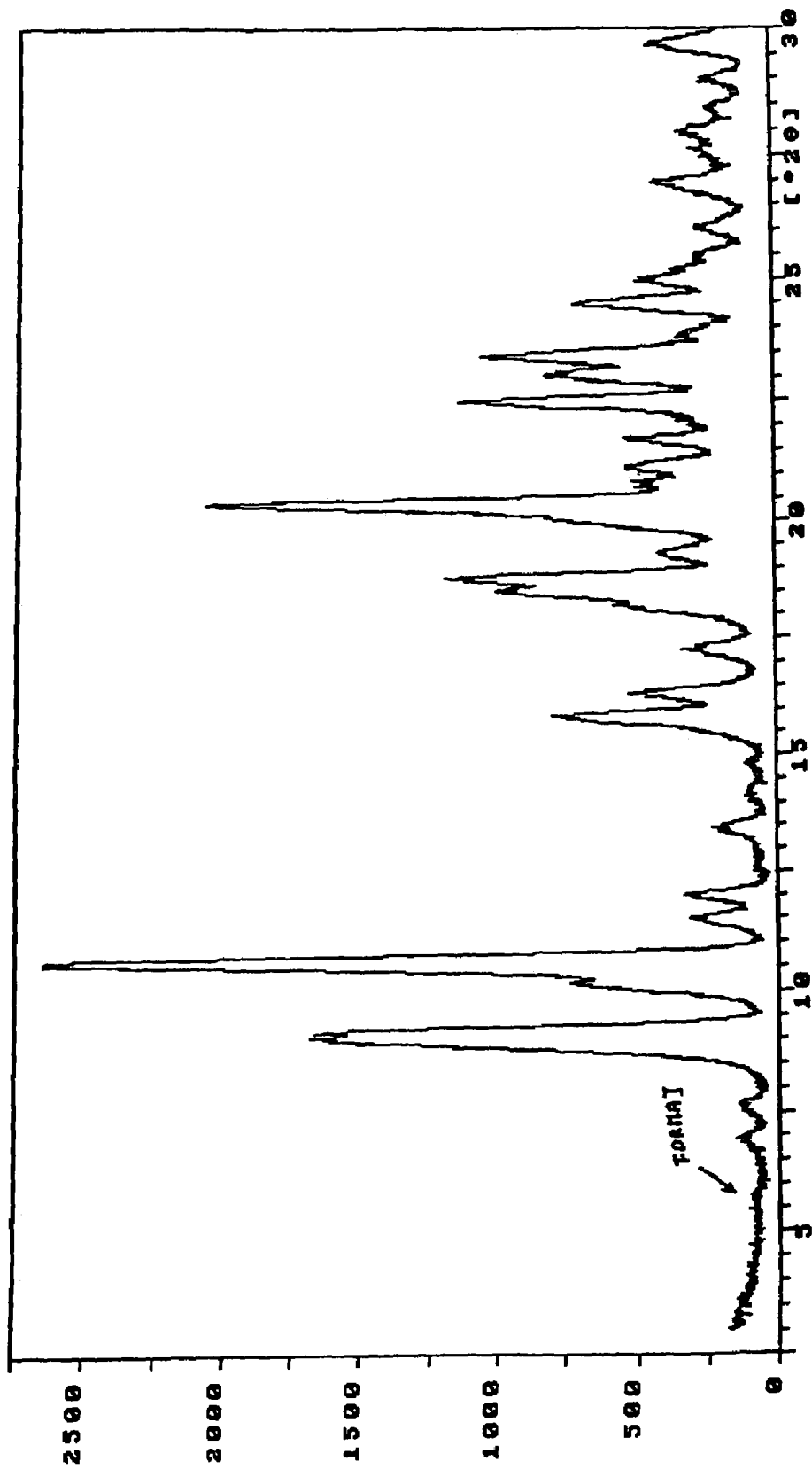
FIG. 18: X-ray diffractogram of powders of form II of torsemide as obtainable through the procedure of the present invention with the addition of 2% (by weight) of form I of torsemide. On the Y axis is represented the intensity (counts), whilst the X axis reports the angle of reflection (in degrees 2 theta) increasing from left to right.

The measurement conditions of the diffractogram of FIG. 18 are summarised in table 9, whilst the details of the diffractogram of FIG. 18 are reported in table 10:

TABLE 9

| Sample identification: | TORSEMIDE II + I (2%) |
|---|---|
| diffractometer type: | PW1710 BASED |
| Tube Anode: | Cu |
| Generator tension [kV]: | 40 |
| Generator current [mA]: | 40 |
| Wavelength alpha1 [Å]: | 1.54051 |
| Wavelength alpha2 [Å]: | 1.54439 |
| Intensity ratio (alpha2/alpha1): | 0.500 |
| Divergence slit: | 1° |
| Receiving slit: | 0.1 |
| Monochromator used: | YES |
| Start angle [°2θ]: | 3.000 |
| End angle [°2θ]: | 30.000 |
| Step size [°2θ]: | 0.010 |
| Maximum intensity: | 2460.160 |
| time per step [s]: | 0.700 |
| type of scan: | STEP |
| Minimum peak tip width: | 0.00 |
| Maximum peak tip width: | 1.00 |
| Peak base width: | 2.00 |
| Minimum significance: | 0.75 |
| Number of peaks: | 42 |

TABLE 10

| Angle [° 2θ] | Value d α1 [Å] | Value d α2 [Å] | Peak width [° 2θ] | Peak intensity [counts] | Base intensity [counts] | Relative intensity [%] | Significance |
|---|---|---|---|---|---|---|---|
| 5.620 | 15.7118 | 15.7513 | 0.480 | 12 | 72 | 0.5 | 2.03 |
| 6.960 | 12.6895 | 12.7215 | 0.120 | 48 | 69 | 1.9 | 1.07 |
| 7.695 | 11.4790 | 11.5079 | 0.050 | 64 | 69 | 2.6 | 0.83 |
| 9.025 | 9.7901 | 9.8148 | 0.140 | 1552 | 69 | 63.1 | 4.54 |
| 9.260 | 9.5422 | 9.5662 | 0.040 | 1116 | 69 | 45.3 | 0.81 |
| 10.160 | 8.6989 | 8.7208 | 0.120 | 671 | 69 | 27.3 | 1.99 |
| 10.655 | 8.2958 | 8.3167 | 0.050 | 2460 | 69 | 100.0 | 1.24 |
| 11.480 | 7.7014 | 7.7208 | 0.200 | 219 | 69 | 8.9 | 8.36 |
| 11.970 | 7.3873 | 7.4059 | 0.260 | 234 | 69 | 9.5 | 20.19 |
| 13.425 | 6.5897 | 6.6063 | 0.160 | 132 | 69 | 5.4 | 3.60 |
| 14.210 | 6.2274 | 6.2431 | 0.320 | 28 | 69 | 1.1 | 5.09 |
| 14.810 | 5.9764 | 5.9915 | 0.160 | 24 | 69 | 1.0 | 0.87 |
| 15.690 | 5.6432 | 5.6574 | 0.100 | 543 | 69 | 22.1 | 1.33 |
| 15.850 | 5.5865 | 5.6006 | 0.050 | 676 | 69 | 27.5 | 0.98 |
| 16.325 | 5.4251 | 5.4387 | 0.040 | 433 | 69 | 17.6 | 1.03 |
| 16.425 | 5.3922 | 5.4058 | 0.060 | 292 | 69 | 11.9 | 0.86 |
| 17.330 | 5.1126 | 5.1255 | 0.060 | 213 | 69 | 8.7 | 0.82 |
| 18.090 | 4.8995 | 4.9119 | 0.100 | 400 | 69 | 16.3 | 0.81 |
| 18.500 | 4.7919 | 4.8039 | 0.160 | 918 | 69 | 37.3 | 5.04 |
| 18.765 | 4.7248 | 4.7367 | 0.200 | 1082 | 69 | 44.0 | 17.90 |
| 19.280 | 4.5997 | 4.6113 | 0.160 | 353 | 69 | 14.4 | 2.54 |
| 19.880 | 4.4622 | 4.4735 | 0.160 | 497 | 69 | 20.2 | 1.03 |
| 20.320 | 4.3666 | 4.3776 | 0.060 | 1858 | 69 | 75.5 | 0.87 |
| 20.425 | 4.3444 | 4.3553 | 0.040 | 1648 | 69 | 67.0 | 0.91 |
| 20.800 | 4.2669 | 4.2776 | 0.080 | 420 | 69 | 17.1 | 0.81 |
| 21.125 | 4.2020 | 4.2126 | 0.140 | 458 | 69 | 18.6 | 3.04 |
| 21.735 | 4.0854 | 4.0957 | 0.040 | 458 | 69 | 18.6 | 0.80 |
| 22.385 | 3.9682 | 3.9782 | 0.080 | 767 | 69 | 31.2 | 0.78 |
| 22.490 | 3.9499 | 3.9599 | 0.160 | 1011 | 69 | 41.1 | 10.43 |
| 23.030 | 3.8585 | 3.8682 | 0.180 | 697 | 69 | 28.3 | 6.51 |
| 23.420 | 3.7951 | 3.8047 | 0.180 | 961 | 69 | 39.1 | 11.99 |
| 23.895 | 3.7208 | 3.7301 | 0.160 | 246 | 69 | 10.0 | 0.99 |
| 24.490 | 3.6317 | 3.6408 | 0.220 | 635 | 69 | 25.8 | 17.48 |
| 24.950 | 3.5658 | 3.5748 | 0.060 | 400 | 69 | 16.3 | 0.92 |
| 25.525 | 3.4867 | 3.4955 | 0.060 | 196 | 69 | 8.0 | 0.78 |
| 26.050 | 3.4176 | 3.4262 | 0.120 | 196 | 69 | 8.0 | 1.86 |
| 26.935 | 3.3073 | 3.3157 | 0.160 | 357 | 69 | 14.5 | 5.44 |
| 27.610 | 3.2280 | 3.2361 | 0.120 | 199 | 69 | 8.1 | 0.88 |
| 27.960 | 3.1884 | 3.1964 | 0.100 | 253 | 69 | 10.3 | 1.16 |
| 28.430 | 3.1367 | 3.1446 | 0.240 | 151 | 59 | 6.1 | 4.17 |
| 29.015 | 3.0748 | 3.0825 | 0.180 | 174 | 69 | 7.1 | 4.17 |
| 29.690 | 3.0064 | 3.0140 | 0.160 | 350 | 69 | 14.2 | 4.48 |

Figure 19:
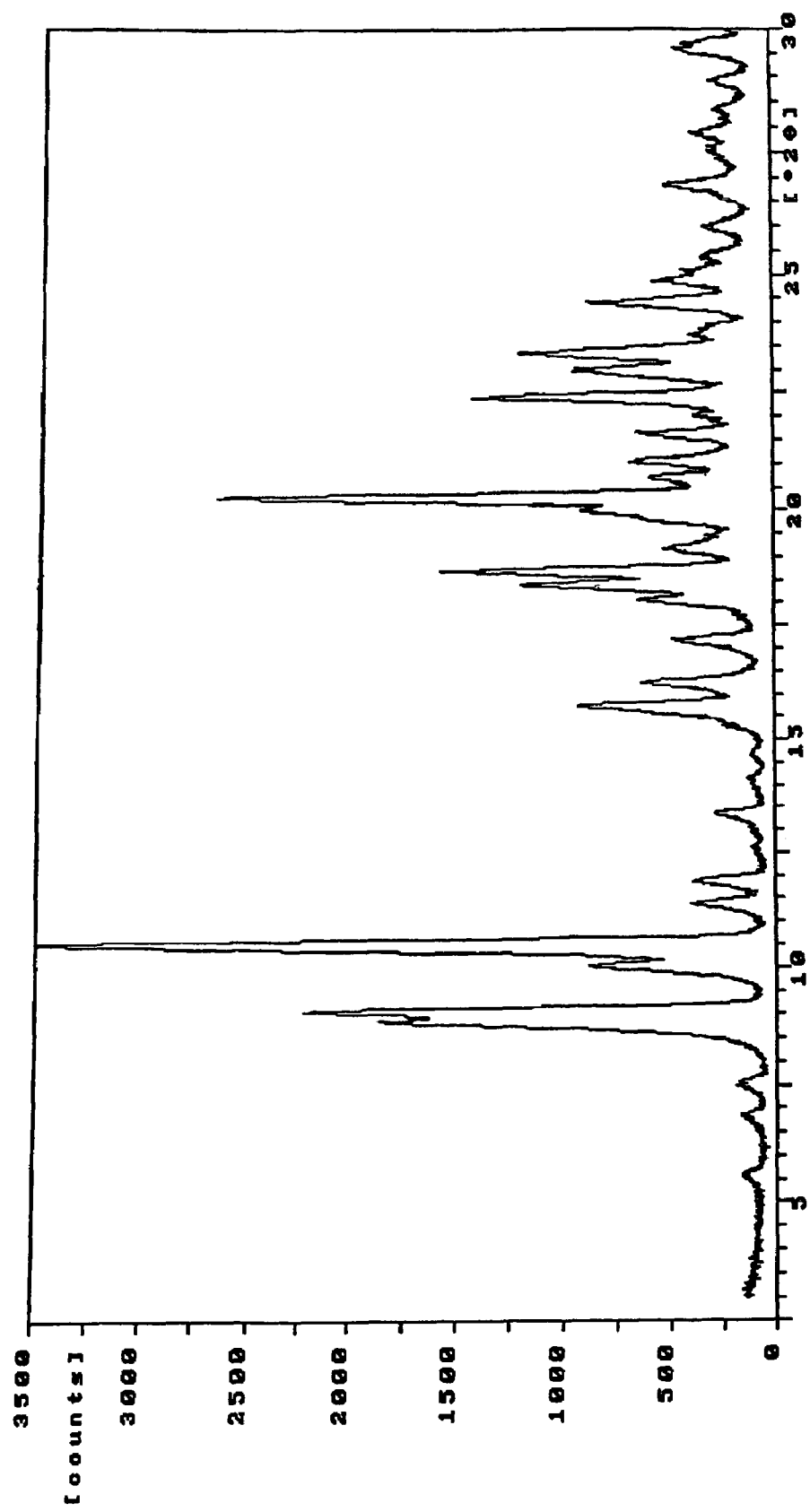
FIG. 19: X-ray diffractogram of powders of form II of torsemide as obtainable through the procedure of the present invention with the addition of 4% (by weight) of form I of torsemide. On the Y axis is represented the intensity (counts), whilst the X axis reports the angle of reflection (in degrees 2 theta) increasing from left to right.

The X-ray diffractogram of the powders of the sample of form II of torsemide contaminated with 4% of form I is represented in FIG. 19.

The measurement conditions of the diffractogram of FIG. 19 are summarised in table 11, whilst the details of the diffractogram of FIG. 19 are reported in table 12:

TABLE 11

| Sample identification: | TORSEMIDE II + I (4%) |
|---|---|
| diffractometer type: | PW1710 BASED |
| Tube Anode: | Cu |
| Generator tension [kV]: | 40 |
| Generator current [mA]: | 40 |
| Wavelength alpha1 [Å]: | 1.54051 |
| Wavelength alpha2 [Å]: | 1.54439 |

TABLE 11-continued

| Intensity ratio (alpha2/alpha1): | 0.500 |
|---|---|
| Divergence slit: | 1° |
| Receiving slit: | 0.1 |
| Monochromator used: | YES |
| Start angle [°2θ]: | 3.000 |
| End angle [°2θ]: | 30.000 |
| Step size [°2θ]: | 0.010 |
| Maximum intensity: | 3422.250 |
| time per step [s]: | 0.7000 |
| type of scan: | STEP |
| Minimum peak tip width: | 0.00 |
| Maximum peak tip width: | 1.00 |
| Peak base width: | 2.00 |
| Minimum significance: | 0.75 |
| Number of peaks: | 47 |

TABLE 12

| Angle [° 2θ] | Value d α1 [Å] | Value d α2 [Å] | Peak width [° 2θ] | Peak intensity [counts] | Base intensity [counts] | Relative intensity [%] | Significance |
|---|---|---|---|---|---|---|---|
| 3.320 | 26.5895 | 26.6564 | 0.640 | 52 | 69 | 1.5 | 2.86 |
| 5.595 | 15.7819 | 15.8217 | 0.100 | 88 | 69 | 2.6 | 1.25 |
| 6.860 | 12.8743 | 12.9067 | 0.120 | 85 | 69 | 2.5 | 2.35 |
| 7.595 | 11.6299 | 11.6592 | 0.080 | 98 | 69 | 2.9 | 0.92 |
| 8.805 | 10.0343 | 10.0595 | 0.050 | 1568 | 69 | 45.8 | 0.91 |
| 8.870 | 9.9609 | 9.9860 | 0.030 | 1789 | 69 | 52.3 | 0.78 |
| 9.070 | 9.7417 | 9.7662 | 0.140 | 2116 | 69 | 61.8 | 30.22 |
| 9.970 | 8.8642 | 8.8865 | 0.060 | 697 | 69 | 20.4 | 1.19 |
| 10.475 | 8.4380 | 8.4592 | 0.080 | 3283 | 69 | 95.9 | 2.71 |
| 10.515 | 8.4060 | 8.4271 | 0.080 | 3422 | 69 | 100.0 | 7.06 |
| 11.395 | 7.7587 | 7.7782 | 0.070 | 292 | 69 | 8.5 | 1.35 |
| 11.890 | 7.4368 | 7.4555 | 0.220 | 296 | 69 | 8.6 | 21.10 |
| 12.590 | 7.0248 | 7.0425 | 0.240 | 24 | 69 | 0.7 | 2.14 |
| 13.355 | 6.6241 | 6.6408 | 0.070 | 219 | 69 | 6.4 | 1.24 |
| 14.145 | 6.2559 | 6.2716 | 0.120 | 44 | 69 | 1.3 | 1.56 |
| 14.690 | 6.0250 | 6.0402 | 0.140 | 41 | 69 | 1.2 | 1.53 |
| 15.805 | 5.6024 | 5.6165 | 0.030 | 681 | 69 | 19.9 | 0.87 |
| 16.250 | 5.4499 | 5.4636 | 0.160 | 543 | 69 | 15.9 | 12.37 |
| 17.180 | 5.1569 | 5.1699 | 0.160 | 400 | 69 | 11.7 | 10.15 |
| 18.070 | 4.9049 | 4.9173 | 0.040 | 586 | 69 | 17.1 | 0.88 |
| 18.380 | 4.8229 | 4.8350 | 0.050 | 1129 | 69 | 33.0 | 1.04 |
| 18.440 | 4.8073 | 4.8194 | 0.030 | 1069 | 69 | 31.2 | 0.97 |
| 18.700 | 4.7411 | 4.7530 | 0.050 | 1498 | 69 | 43.8 | 1.43 |
| 19.185 | 4.6223 | 4.6339 | 0.180 | 433 | 69 | 12.6 | 8.00 |
| 19.755 | 4.4902 | 4.5015 | 0.120 | 484 | 69 | 14.1 | 2.18 |
| 20.000 | 4.4357 | 4.4469 | 0.100 | 835 | 69 | 24.4 | 1.65 |
| 20.280 | 4.3751 | 4.3861 | 0.150 | 2500 | 69 | 73.1 | 34.39 |
| 20.705 | 4.2863 | 4.2970 | 0.140 | 511 | 69 | 14.9 | 6.37 |
| 21.095 | 4.2079 | 4.2185 | 0.060 | 534 | 69 | 15.6 | 1.14 |
| 21.630 | 4.1050 | 4.1153 | 0.160 | 552 | 69 | 16.1 | 11.31 |
| 22.040 | 4.0295 | 4.0397 | 0.100 | 292 | 69 | 8.5 | 1.87 |
| 22.400 | 3.9656 | 3.9756 | 0.060 | 1362 | 69 | 39.8 | 2.35 |
| 22.460 | 3.9551 | 3.9651 | 0.060 | 1082 | 69 | 31.6 | 1.65 |
| 22.980 | 3.8668 | 3.8765 | 0.160 | 841 | 69 | 24.6 | 9.15 |
| 23.340 | 3.8080 | 3.8176 | 0.050 | 1142 | 69 | 33.4 | 1.30 |
| 23.775 | 3.7393 | 3.7487 | 0.240 | 299 | 69 | 8.7 | 3.98 |
| 24.420 | 3.6419 | 3.6511 | 0.040 | 734 | 69 | 21.5 | 1.10 |
| 24.865 | 3.5778 | 3.5868 | 0.030 | 488 | 69 | 14.3 | 0.97 |
| 25.365 | 3.5084 | 3.5172 | 0.120 | 253 | 69 | 7.4 | 1.56 |
| 25.990 | 3.4254 | 3.4340 | 0.200 | 246 | 69 | 7.2 | 7.83 |
| 26.845 | 3.3182 | 3.3266 | 0.180 | 437 | 69 | 12.8 | 10.20 |
| 27.540 | 3.2360 | 3.2442 | 0.160 | 219 | 69 | 6.4 | 1.34 |
| 27.890 | 3.1962 | 3.2043 | 0.080 | 286 | 69 | 8.3 | 0.82 |
| 28.375 | 3.1427 | 3.1506 | 0.100 | 193 | 69 | 5.6 | 1.19 |
| 28.950 | 3.0815 | 3.0893 | 0.120 | 210 | 69 | 6.1 | 2.46 |
| 29.580 | 3.0173 | 3.0249 | 0.180 | 380 | 69 | 11.1 | 6.90 |
| 29.695 | 3.0059 | 3.0135 | 0.120 | 346 | 69 | 10.1 | 2.66 |

Figure 20:
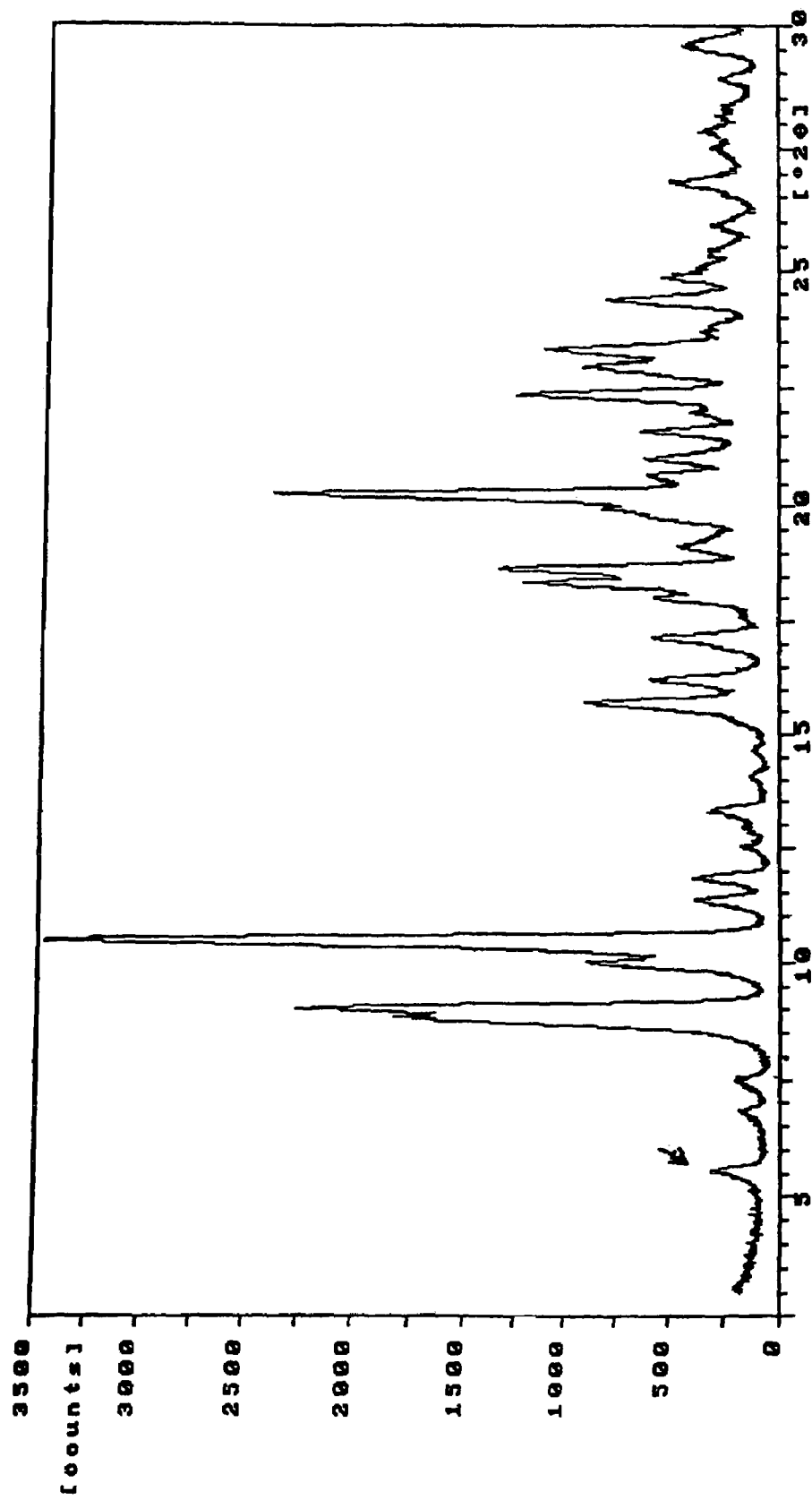
FIG. 20: X-ray diffractogram of powders of form II of torsemide as obtainable through the procedure of the present invention with the addition of 8% (by weight) of form I of torsemide. On the Y axis is represented the intensity (counts), whilst the X axis reports the angle of reflection (in degrees 2 theta) increasing from left to right.

The X-ray diffractogram of the powders of the sample of form II of torsemide contaminated with 8% of form I is represented in FIG. 20. The measurement conditions of the diffractogram of FIG. 20 correspond to these of FIG. 19. In FIG. 20, the signal at approx. 5.7° two theta countersigning the presence of form I of torsemide (8% by weight) in the sample of form II of torsemide is easily detectable.

In particular, from FIGS. 18–20 it appears that whilst a contamination of 4%–8% of form I of torsemide in a sample of form II of torsemide is easily identifiable in the tests by the presence of a signal at 5.7° two theta (a characteristic signature for form I) in the X-ray diffractogram of the powders, instead a contamination of 2% or less is identifiable with difficulty. It is thus concluded that the achievable detection threshold with X-ray diffraction of the powders amounts to 2% (by weight) of form I of torsemide in a sample of pure form II of torsemide. In particular, it is seen that the signal at approx. 5.7° two theta, characteristic of form I of torsemide, is confused with the background noise in the X-ray diffractogram of the powders, if the contamination by form I in a sample of pure form II is less than 2% by weight.

Example 3b

FT-IR-Perkin Elmer

Figure 27:
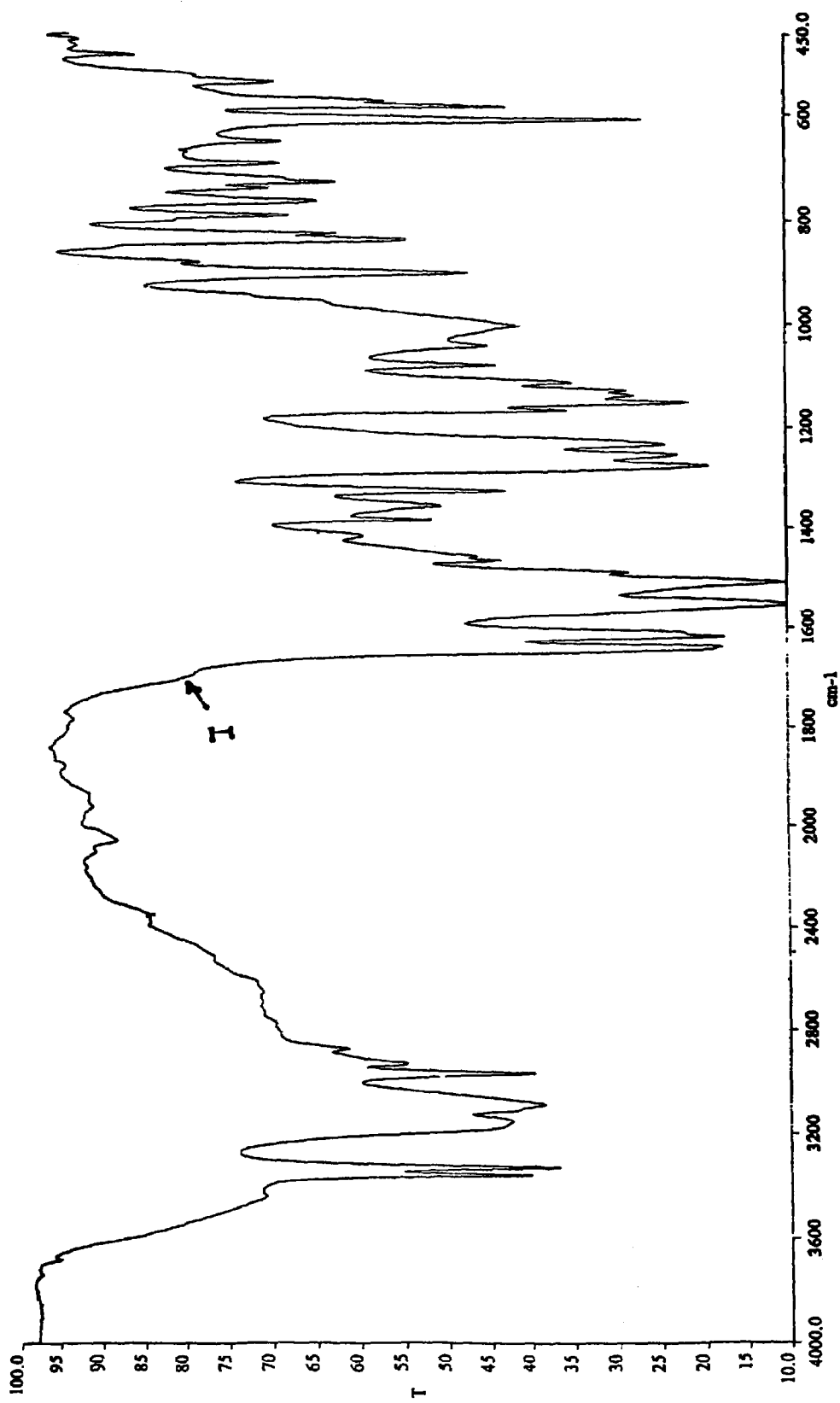
FIG. 27: FT-IR spectrum (Perkin Elmer) of form II of torsemide as obtainable through the procedure in the present invention with the addition of 1% (by weight) of form I of torsemide. On the Y axis is represented the transmittance (in %), whilst the X axis reports the wave number (in cm$^{-1}$).
Figure 28:
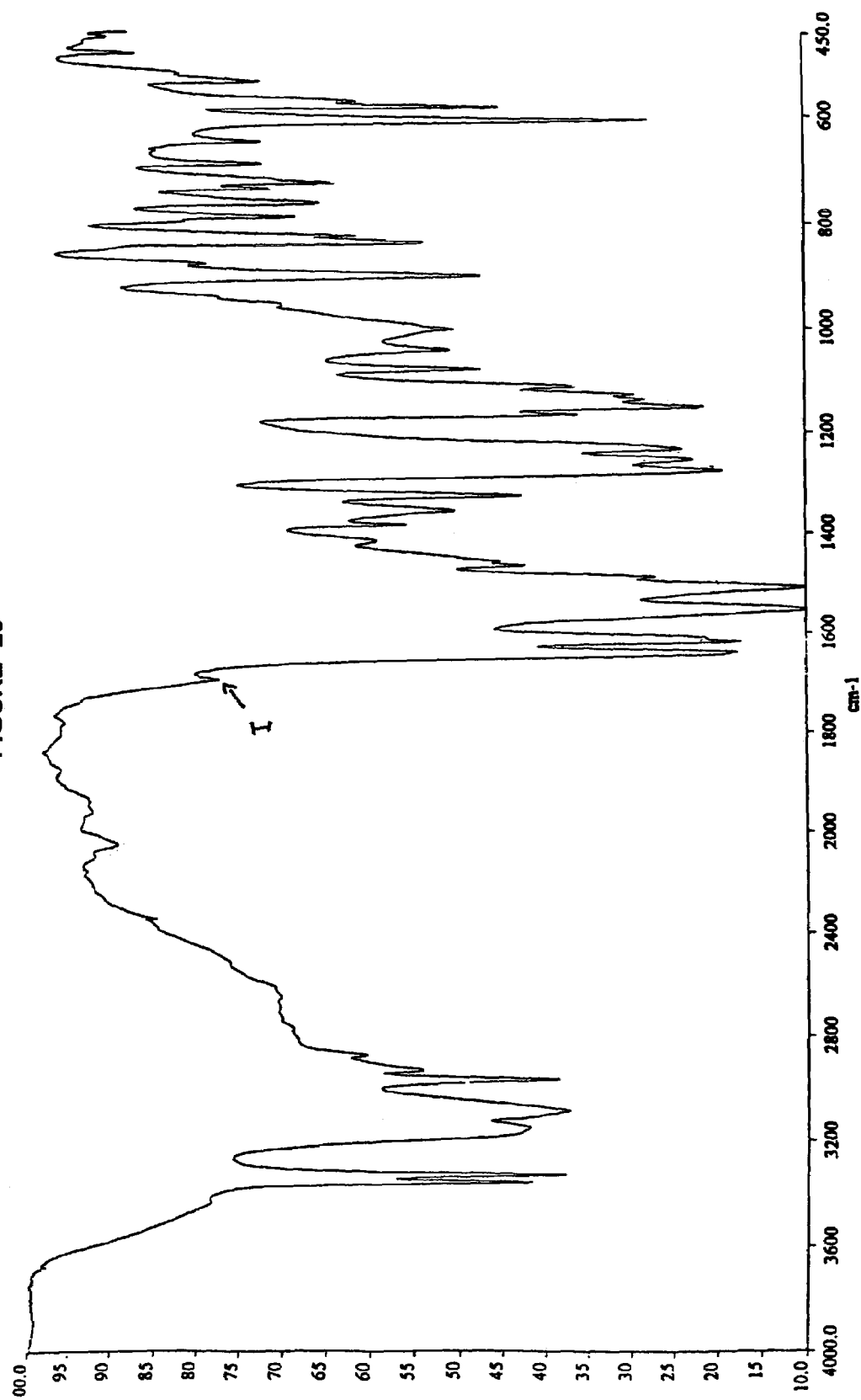
FIG. 28: FT-IR spectrum (Perkin Elmer) of form II of torsemide as obtainable through the procedure of the present invention with the addition of 4% (by weight) of form I of torsemide. On the Y axis is represented the transmittance (in %), whilst the X axis reports the number of waves (in cm$^{-1}$).

In this example, there have been added, respectively 1% and 4% by weight of form I of torsemide to a sample of form II of torsemide obtainable through the method of the present invention. The FT-IR spectrum (Perkin Elmer) of form II of torsemide obtainable through the method of the present invention with the addition of 1% (by weight) of form I of torsemide is represented in FIG. 27. The FT-IR spectrum (Perkin Elmer) of form II of torsemide as obtained through the method of the present invention with the addition of 4% (by weight) of form I of torsemide is represented in FIG. 28. As is apparent from FIG. 27 and 28 one sees that the achievable detection threshold through evaluation of the FT-IR spectrum in KBr amounts to 1% (by weight) of form I of torsemide in a sample of pure form II of torsemide. In particular, it is seen that the peak at 1697 cm$^{-1}$, characteristic of form I of torsemide, becomes perceptible at least as a "shoulder" of the adjacent peak in the FT-IR spectrum in KBr, if the contamination by form I in a sample of pure form II is equal to or greater than 1% by weight.

Example 3c

FT-IR Jasco

Figure 21:
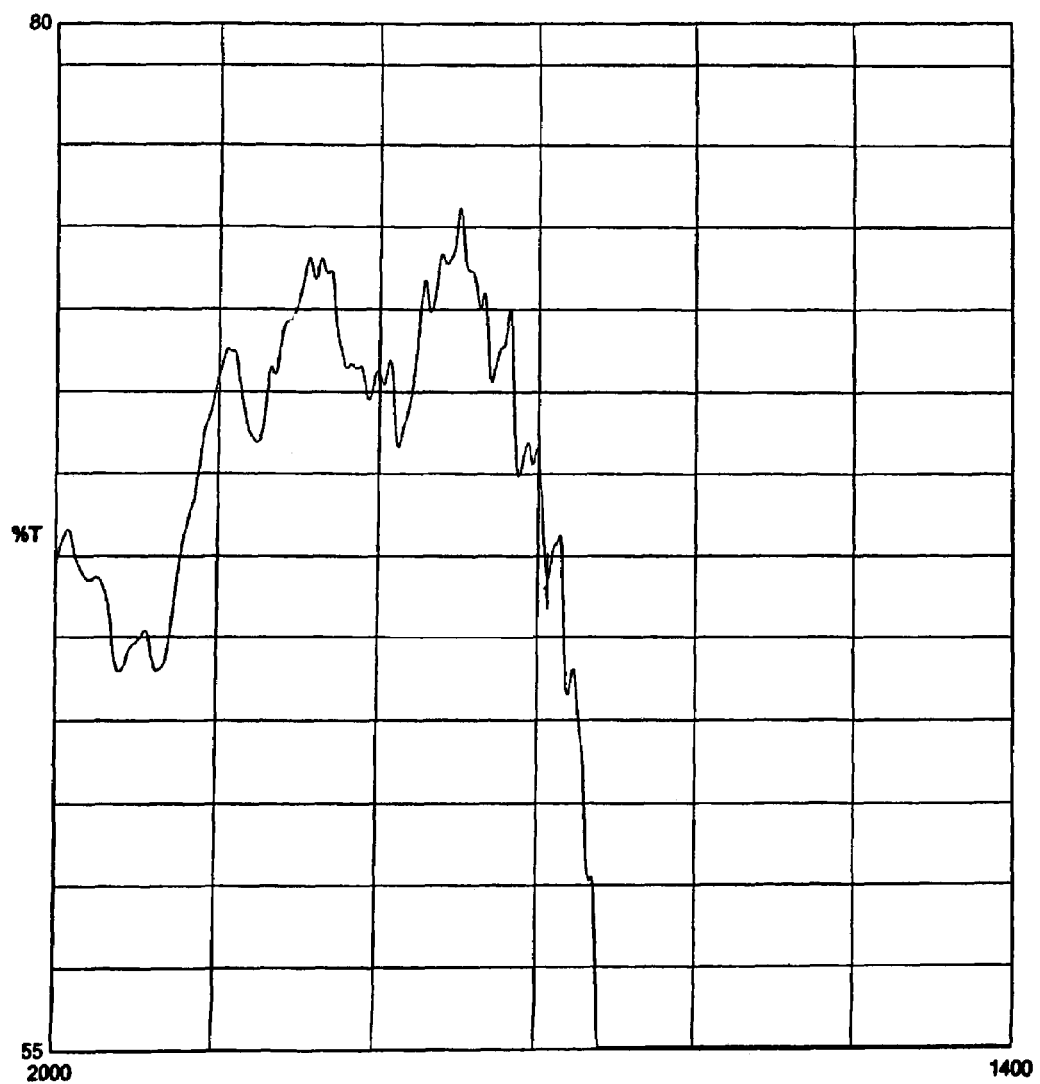
FIG. 21: FT-IR spectrum (Jasco) enlarged between 2000 and 1400 cm$^{-1}$ of form II of torsemide as obtainable through the procedure of the present invention. On the Y axis is represented the transmittance (in %), whilst the X axis reports the wave number (in cm$^{-1}$).
Figure 22:
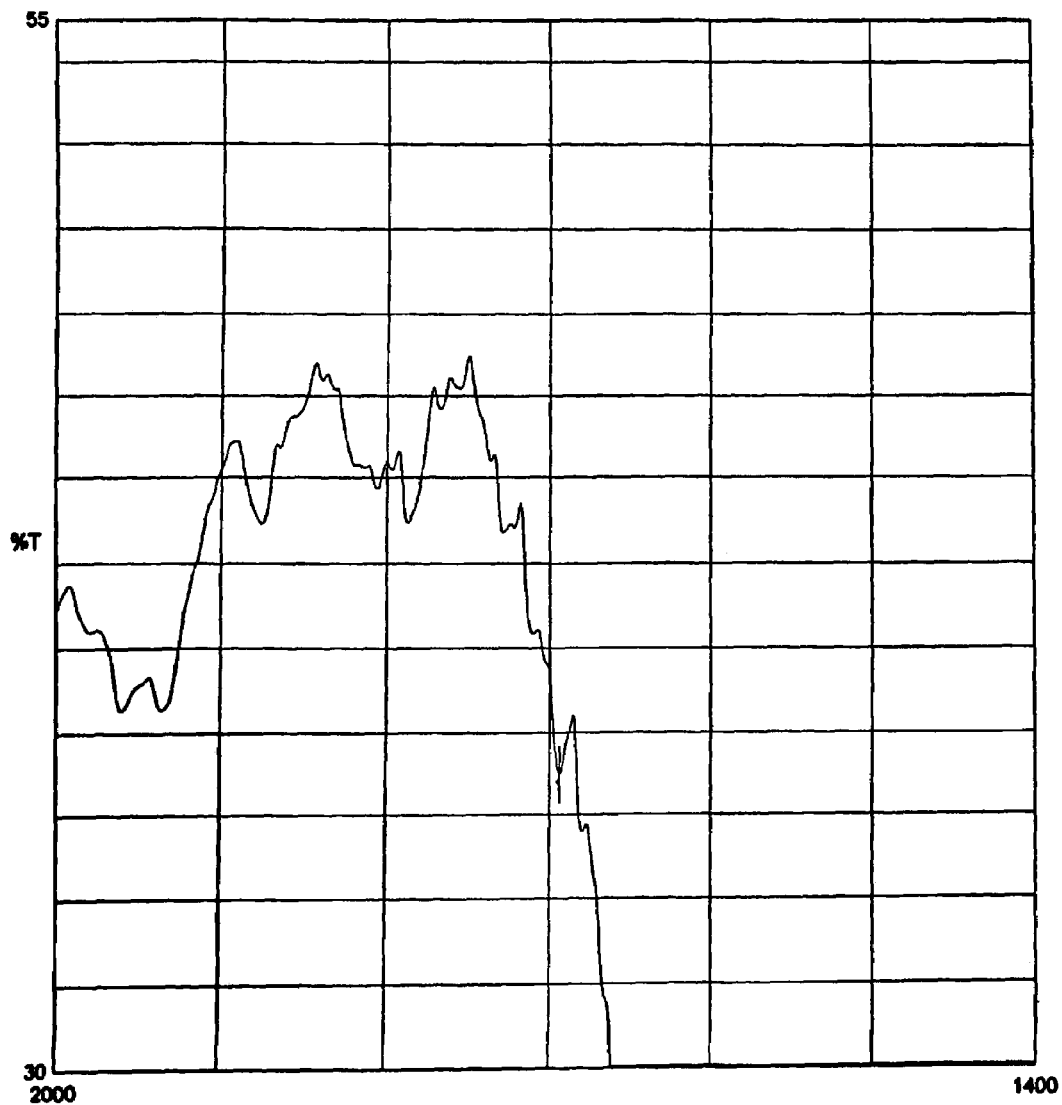
FIG. 22: FT-IR spectrum (Jasco) enlarged between 2000 and 1400 cm$^{-1}$ of form II of torsemide as available through the procedure of the present invention with the addition of 1% (by weight) of form I. On the Y axis is represented the transmittance (in %), whilst the X axis reports the wave number (in cm$^{-1}$).
Figure 23:
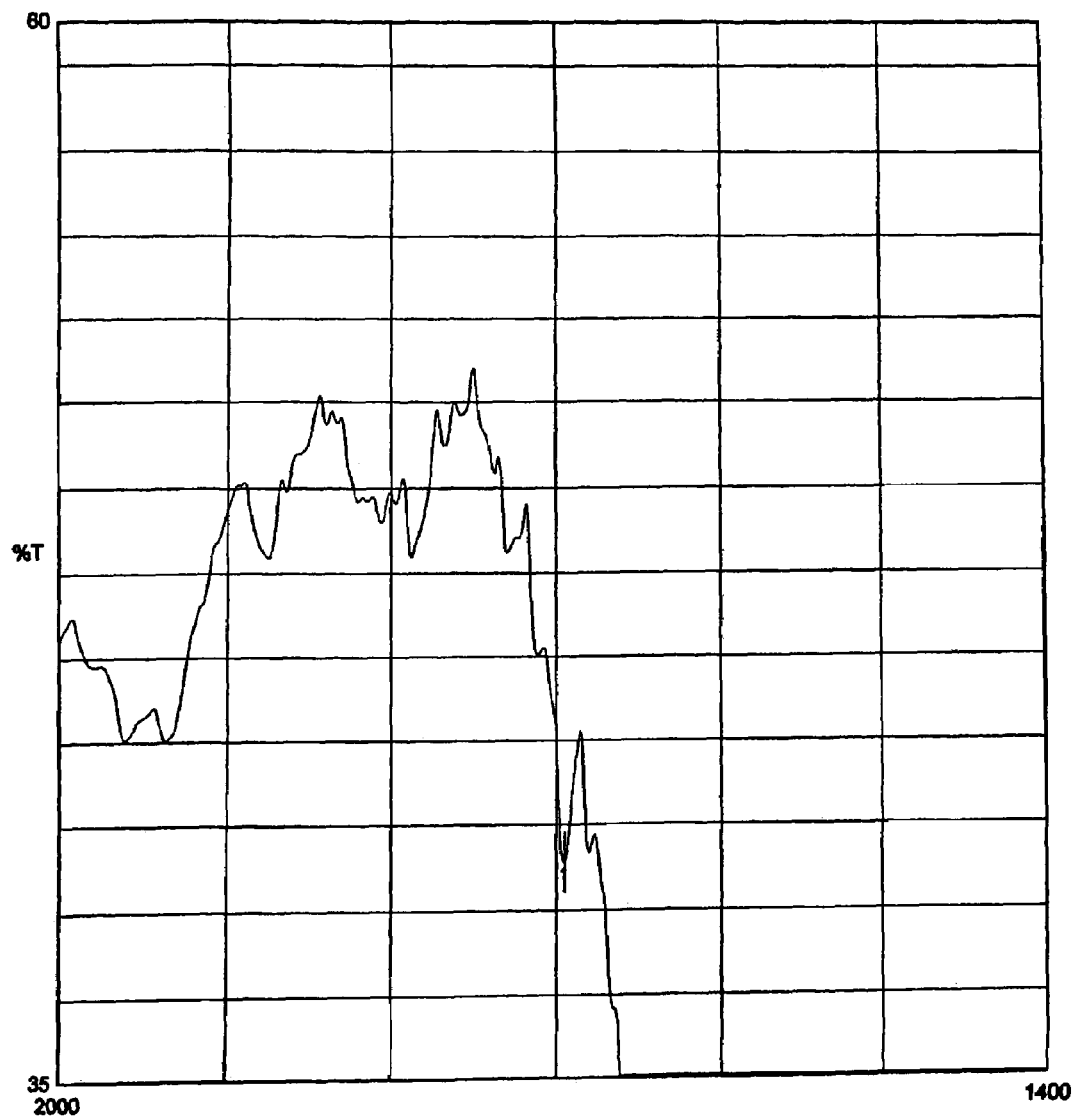
FIG. 23: FT-IR spectrum (Jasco) enlarged between 2000 and 1400 cm$^{-1}$ of form II of torsemide as obtainable through the procedure of the present invention with the addition of 3% (by weight) of form I of torsemide. On the Y axis is represented the transmittance (in %), whilst the X axis reports the wave number (in cm$^{-1}$).
Figure 24:
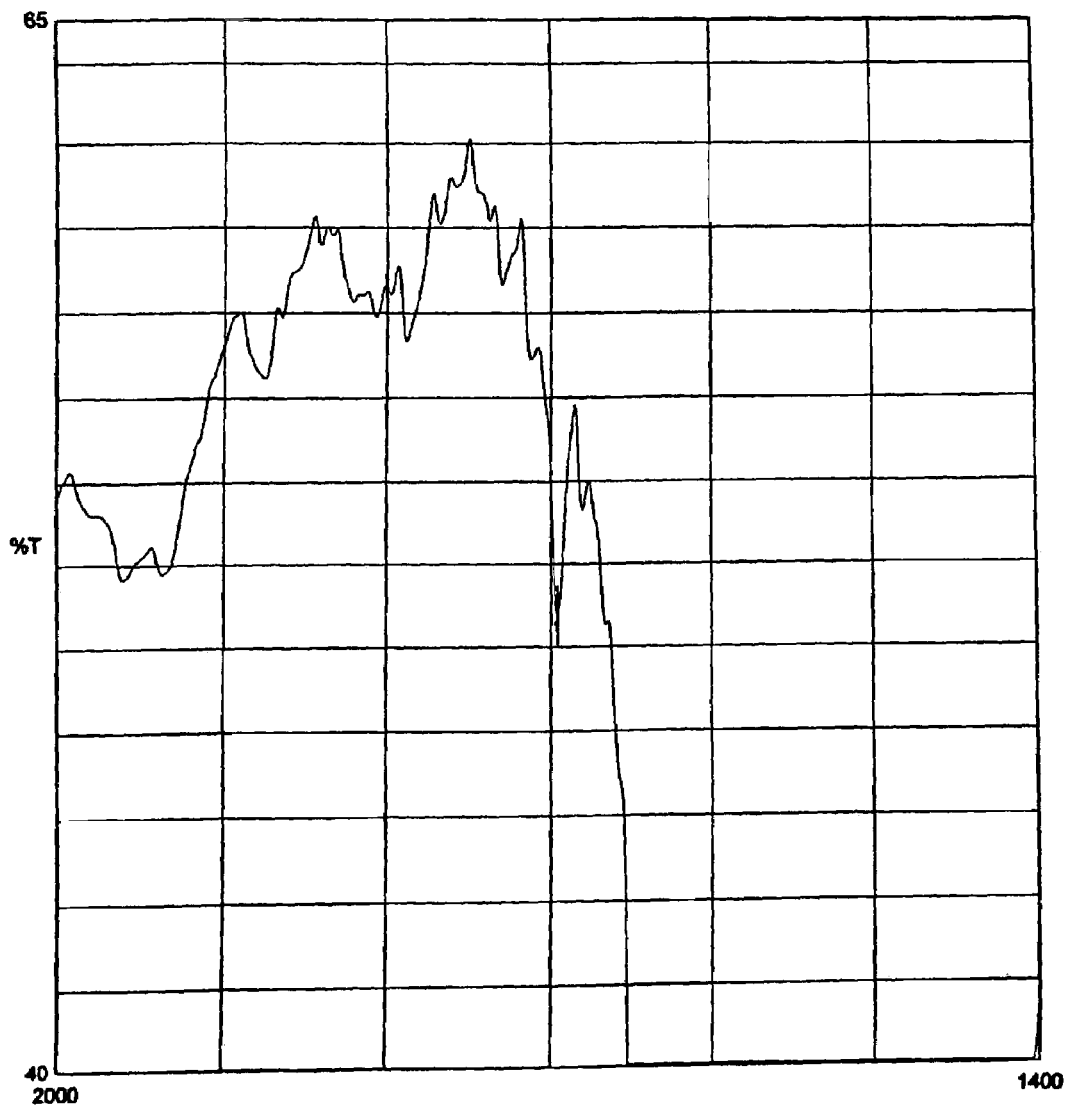
FIG. 24: FT-IR spectrum (Jasco) enlarged between 2000 and 1400 cm$^{-1}$ of form II of torsemide as obtainable through the procedure of the present invention with the addition of 5% (by weight) of form I of torsemide. On the Y axis is represented the transmittance (in %), whilst the X axis reports the wave number (in cm$^{-1}$).
Figure 25:
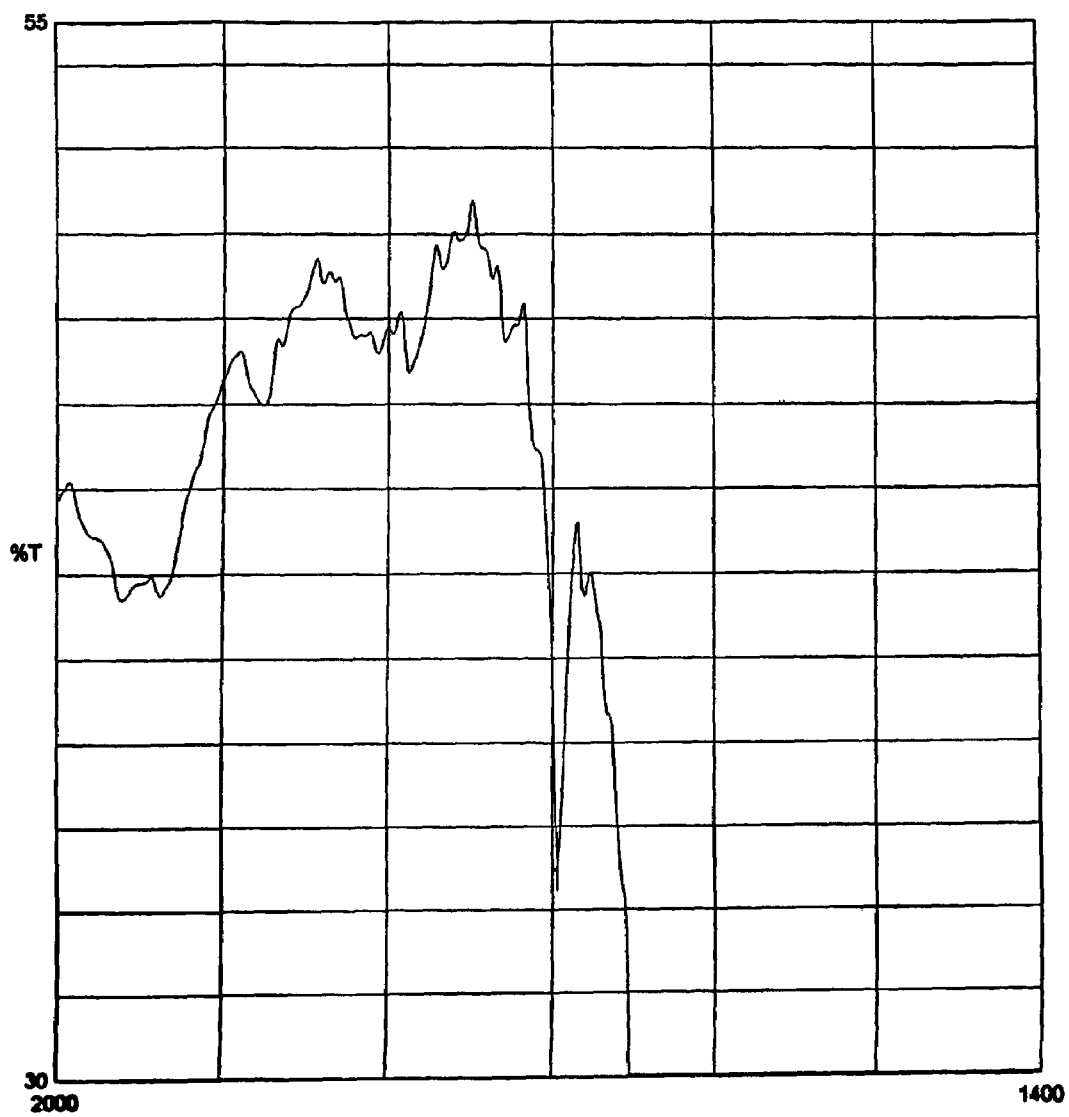
FIG. 25: FT-IR spectrum (Jasco) enlarged between 2000 and 1400 cm$^{-1}$ of form II of torsemide as obtainable through the procedure of the present invention with the addition of 10% (by weight) of torsemide form I. On the Y axis is represented the transmittance (in %), whilst the X axis reports the wave number (in cm$^{-1}$).
Figure 26:
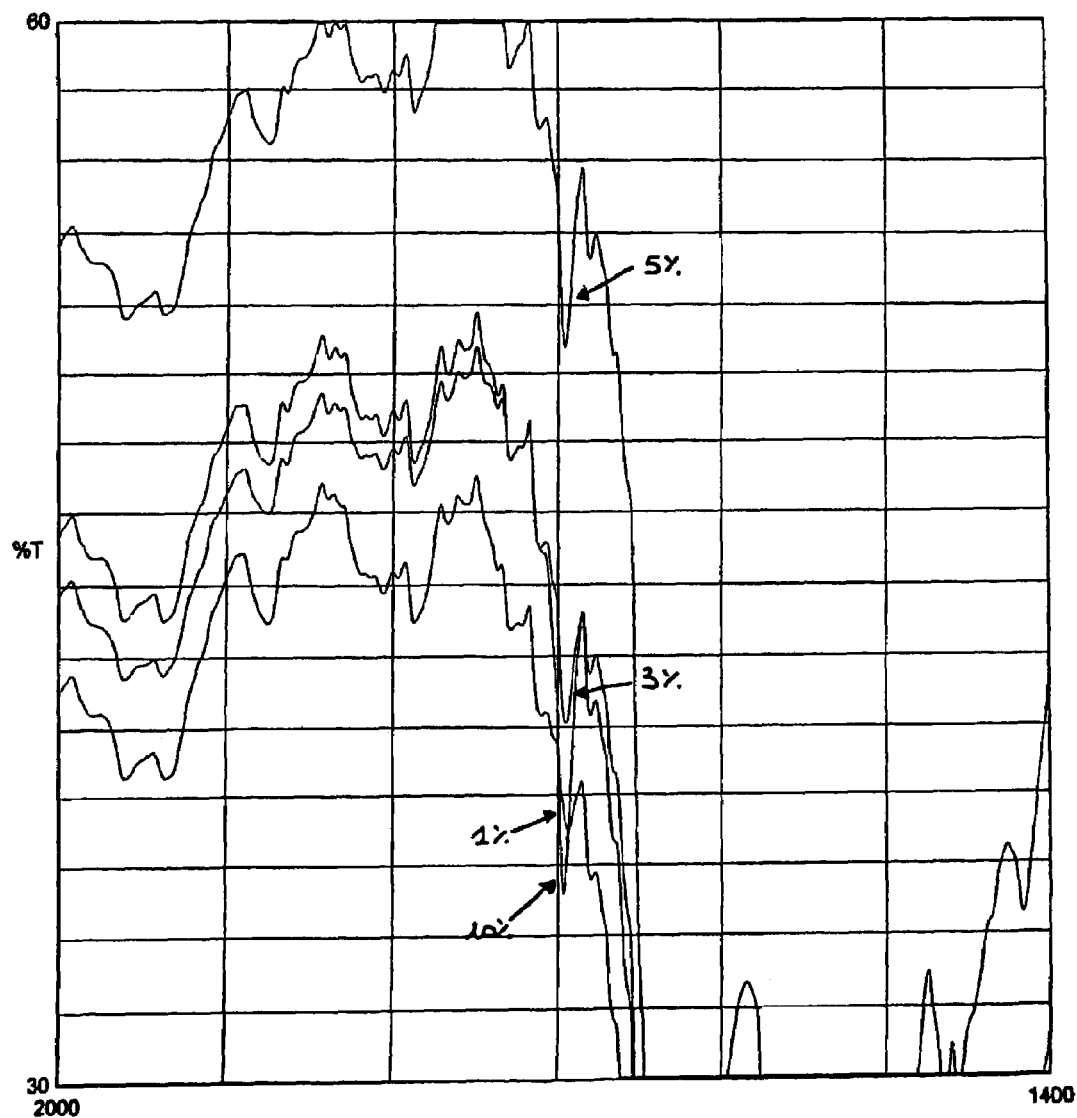
FIG. 26: FT-IR spectrum (Jasco) enlarged between 2000 and 1400 cm$^{-1}$ of form II of torsemide as obtainable through the procedure of the present invention with the addition (for comparison) of 1%, 3%, 5% and 10% (by weight) of torsemide form I. On the Y axis is represented the transmittance (in %), whilst the X axis reports the wave number (in cm$^{-1}$).

In this example, there have been added, respectively 1%, 3%, 5% and 10% by weight of form I of torsemide to a sample of pure form II of torsemide obtainable through the method of the present invention. The FT-IR spectrum (Jasco) of form II of torsemide as obtainable through the method of the present invention with the addition of 1% (by weight) of form I of torsemide is represented in FIG. 22. The FT-IR spectrum (Jasco) of form II of torsemide as obtainable through the method of the present invention with the addition of 3% (by weight) of form I of torsemide is represented in FIG. 23. The FT-IR spectrum (Jasco) of form II of torsemide as obtainable through the method of the present invention with the addition of 5% (by weight) of form I of torsemide is represented in FIG. 24. The FT-IR spectrum (Jasco) of form II of torsemide as obtainable through the method of the present invention with the addition of 10% (by weight) of form I of torsemide is represented in FIG. 25. A presentation comparing the FT-IR spectra (Jasco) of form II of torsemide as obtainable through the method of the present invention with the addition of 1%, 3%, 5% and 10% (by weight) of form I of torsemide is represented in FIG. 26. As is apparent from FIGS. 22–26 if compared, respectively, to FIGS. 4 and 21 (the later constituting an enlargement), one sees that the achievable detection threshold through the evaluation of the FT-IR spectra in KBr amounts to 1%, and in the best conditions to 0.5% (by weight) of form I of torsemide in a sample of pure form II of torsemide. In particular, it is seen that the peak at approx. 1697 cm$^{-1}$, characteristic of form I of torsemide, becomes perceptible, at least as a "shoulder" of the adjacent peak in the FT-IR spectrum in KBr, if the contamination by form I in a sample of pure form II is equal to or greater than 1% by weight. One presumes that with the Jasco apparatus, the detectability of form I in form II, in very favourable conditions can be reduced to 0.5%–0.3% by weight.

The measurement conditions of the FT-IR spectrum of the FIGS. 21–26 are summarised in table 13.

TABLE 13

| Accumulation | 32 volts |
|---|---|
| Resolution | 4 cm$^{-1}$ |
| Apodisation | Cosine |
| Sample name | Torsemide as per the legend to FIG. 21–26 |
| Gain | 16 |
| Speed | 2.0 mm/sec |
| Delay time | 0 sec |
| Light source | Ni/Cr Filament |
| Detector | 1 |
| Beam splitter | KBr |

Example 4

Stability Tests of Pure Form II of Torsemide:

Example 4a

Accelerated Test with Pure Solid Form II at 40°±2C and 75±5% of Relative Humidity.

This type of test which is prescribed according to ICH (Q1A, "Stability testing of new Drug Substances and new Drug Products", 1$^{st}$ edition Oct. 27, 1997 and 2$^{nd}$ edition Nov. 8, 2000) allows, according to internationally recognised procedures, to extrapolate the results obtained with this accelerated test to a mock storage period at room temperature for over 2 years.

The inventors of the present patent application have subjected a series of pure samples of form II of torsemide to this test, and have assayed with the frequency and to the prescribed terms, the possible polymorphic transformations of the samples through registration of the FT-IR spectra in KBr on a Jasco apparatus. Over 6 months, no detectable polymorphic transformation was witnessed.

Example 4b

Prolonged Test with Pure Solid Form II at 25°±2C and 60±5% of Relative Humidity.

This type of test which is prescribed according to ICH (Q1A, "Stability testing of new Drug Substances and new Drug Products", 1$^{st}$ edition Oct. 27, 1997 and 2$^{nd}$ edition Nov. 8, 2000) follows possible degradation of the samples under more mild conditions, but over prolonged periods. The inventors of the present patent application have subjected a series of pure samples of form II of torsemide to this test, and have assayed with the frequency and to the prescribed terms, the possible polymorphic transformations of the samples through the registration of the FT-IR spectra in KBr on the Jasco apparatus. After 13 months, one could not see any detectable polymorphic transformation.

Example 4c

Drastic Test with Pure Solid Form II at 80° C. for Two Days (Carried Out in the Absence of Light).

In this further test of conformation, it was found that pure and stable form II of torsemide obtainable according to the methods of the present invention does not show a detectable polymorphic transformation if heated at 80° C. for two days.

The invention claimed is:

1. A process for the attainment of pure and stable form II of torsemide comprising the following steps:
   suspension of crude dried torsemide in 10 parts of deionised water,
   the addition of 48% potassium hydrate solution, slowly with stirring maintaining the temperature at 20–25° C., until obtaining complete solution and without exceeding pH 12.5,
   filtration of the solution thus obtained through 40 micron paper,
   gradual acidification of the filtrate thus obtained by stirring with 80% acetic acid preferably until reaching a pH of 5.3–5.7 maintaining the temperature at 20–25° C. during the addition, obtaining a suspension,
   stirring of the suspension for 30 minutes at a temperature of 20–25° C., suction filtration of the solid obtained and washing with water,
   drying of the solid in a dryer under vacuum at a temperature of 50° C.

* * * * *